US012706202B2

(12) United States Patent
Chernov et al.

(10) Patent No.: US 12,706,202 B2
(45) Date of Patent: Aug. 11, 2026

(54) SYSTEMS AND METHODS FOR SEGMENTING DENTAL SCANS

(71) Applicant: Align Technology, Inc., San Jose, CA (US)

(72) Inventors: Vitaliy Vladimirovich Chernov, Moscow (RU); Dmitry Zubatkin, Moscow (RU); Aleksandr Sergeevich Karsakov, Nizhny Novgorod (RU); Mikhail Nikolaevich Rychagov, Moscow (RU); Yury A. Brailov, Moscow (RU); Ekaterina Tolstaya, Moscow (RU); Sergey Borisovich Surov, Zelenogradsk (RU); Dmitry Yurievich Chekh, Moscow (RU)

(73) Assignee: Align Technology, Inc., San Jose, CA (US)

( * ) Notice: Subject to any disclaimer, the term of this patent is extended or adjusted under 35 U.S.C. 154(b) by 1046 days.

(21) Appl. No.: 17/534,420

(22) Filed: Nov. 23, 2021

(65) Prior Publication Data

US 2022/0165388 A1 May 26, 2022

Related U.S. Application Data

(60) Provisional application No. 63/117,426, filed on Nov. 23, 2020.

(51) Int. Cl.
*G16H 20/40* (2018.01)
*A61C 7/00* (2006.01)
(Continued)

(52) U.S. Cl.
CPC ............... *G16H 20/40* (2018.01); *G06T 7/11* (2017.01); *G16H 30/20* (2018.01); *A61C 7/002* (2013.01);
(Continued)

(58) Field of Classification Search
CPC ............ G06T 7/11; G06T 2207/20081; G06T 2207/20084; G06T 2207/20116;
(Continued)

(56) References Cited

U.S. PATENT DOCUMENTS

| | | | |
|---|---|---|---|
| 6,227,850 | B1 | 5/2001 | Chishti et al. |
| 6,227,851 | B1 | 5/2001 | Chishti et al. |

(Continued)

FOREIGN PATENT DOCUMENTS

| | | |
|---|---|---|
| WO | 2020048960 A1 | 3/2020 |

OTHER PUBLICATIONS

Lee, S., et al. "Automated CNN-Based Tooth Segmentation in Cone-Beam CT for Dental Implant Planning" IEEE Access, vol. 8, pp. 50507-50518 (Feb. 2020) available from <https://ieeexplore.ieee.org/abstract/document/9007457> (Year: 2020).*

(Continued)

*Primary Examiner* — Jay Hann
(74) *Attorney, Agent, or Firm* — Shay Glenn LLP

(57) ABSTRACT

Systems and methods for segmenting dental scans. First and second segmented volumes of scan data may be formed, where the first segmented volume may have a lower resolution than the segmented volume. Segmenting scan data may be formed by merging the first segmented volume with the second segmented volume. Merging may include removing teeth labels from the first segmented volume, adjusting a resolution of the first segmented volume to be the same as a resolution of the second segmented volume, and replacing voxels in the first segmented volume with voxels from the second segmented volume. The segmented scan data may be aligned to a digital model of the patient's dentition. The digital model of the patient's dentition may be modified to include the tooth roots from the aligned segmented scan data (Continued)

to form a modified digital model. A treatment plan may be displayed or modified using the modified digital model.

28 Claims, 18 Drawing Sheets
(6 of 18 Drawing Sheet(s) Filed in Color)

(51) Int. Cl.
*G06T 7/11* (2017.01)
*G16H 30/20* (2018.01)

(52) U.S. Cl.
CPC ............... *G06T 2207/20081* (2013.01); *G06T 2207/20084* (2013.01); *G06T 2207/20116* (2013.01); *G06T 2207/30036* (2013.01)

(58) Field of Classification Search
CPC .......... G06T 2207/30036; G16H 20/40; G16H 30/20; A61C 7/002
See application file for complete search history.

(56) References Cited

U.S. PATENT DOCUMENTS 6,299,440 B1 10/2001 Phan et al.
6,318,994 B1 11/2001 Chishti et al.
6,371,761 B1 4/2002 Cheang et al.
6,386,878 B1 5/2002 Pavlovskaia et al.
6,406,292 B1 6/2002 Chishti et al.
6,409,504 B1 6/2002 Jones et al.
6,457,972 B1 10/2002 Chishti et al.
6,488,499 B1 12/2002 Miller
6,514,074 B1 2/2003 Chishti et al.
6,554,611 B2 4/2003 Chishti et al.
6,582,229 B1 6/2003 Miller et al.
6,602,070 B2 8/2003 Miller et al.
6,621,491 B1 9/2003 Baumrind et al.
6,688,886 B2 2/2004 Hughes et al.
6,726,478 B1 4/2004 Isiderio et al.
6,729,876 B2 5/2004 Chishti et al.
6,739,869 B1 5/2004 Taub et al.
6,767,208 B2 7/2004 Kaza
6,783,360 B2 8/2004 Chishti
6,845,175 B2 * 1/2005 Kopelman ........... A61C 9/0046 382/294
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,309,230 B2 12/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,307,221 B2 * 6/2019 Cinader, Jr. ............. A61C 7/00
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,758,322 B2 9/2020 Pokotilov et al.
10,779,718 B2 9/2020 Meyer et al.
10,792,127 B2 10/2020 Kopelman et al.
10,828,130 B2 11/2020 Pokotilov et al.
10,835,349 B2 11/2020 Cramer et al.
10,905,526 B2 * 2/2021 Aamodt ................. A61C 7/002
10,973,611 B2 4/2021 Pokotilov et al.
10,991,091 B2 * 4/2021 Ezhov .................. G06V 10/764
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,259,896 B2 3/2022 Matov et al.
11,776,230 B2 * 10/2023 Jo .......................... G06T 19/20 345/420
12,036,092 B2 * 7/2024 Raby .................... A61C 9/0053
2003/0008259 A1 1/2003 Kuo et al.
2003/0143509 A1 7/2003 Kopelman et al.
2003/0207227 A1 11/2003 Abolfathi
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.

(56) References Cited

U.S. PATENT DOCUMENTS

2016/0310235 A1 10/2016 Derakhshan et al.
2017/0273760 A1 9/2017 Morton et al.
2018/0206940 A1* 7/2018 Kopelman ............ G06T 7/0012
2018/0263733 A1* 9/2018 Pokotilov .............. G16H 20/40
2018/0280118 A1 10/2018 Cramer
2019/0029784 A1 1/2019 Moalem et al.
2019/0053876 A1 2/2019 Sterental et al.
2019/0192259 A1 6/2019 Kopelman et al.
2019/0328487 A1 10/2019 Levin et al.
2019/0328488 A1 10/2019 Levin et al.
2019/0333622 A1 10/2019 Levin et al.
2020/0000552 A1 1/2020 Mednikov et al.
2020/0000554 A1 1/2020 Makarenkova et al.
2020/0000555 A1 1/2020 Yuryev et al.
2020/0085546 A1 3/2020 Li et al.
2020/0085548 A1 3/2020 Reynard et al.
2020/0107915 A1 4/2020 Roschin et al.
2020/0155274 A1 5/2020 Pimenov et al.
2020/0214800 A1 7/2020 Matov et al.
2020/0297458 A1 9/2020 Roschin et al.
2020/0306011 A1 10/2020 Chekhonin et al.
2020/0306012 A1 10/2020 Roschin et al.
2020/0315744 A1 10/2020 Cramer
2020/0360109 A1 11/2020 Gao et al.
2021/0073998 A1 3/2021 Brown et al.
2021/0134436 A1 5/2021 Meyer et al.
2021/0174477 A1 6/2021 Shi et al.
2022/0012888 A1* 1/2022 Chen ......................... G06T 5/30
2022/0361992 A1* 11/2022 Ezhov ..................... G06T 19/00

OTHER PUBLICATIONS

Barone, S., et al. “Creation of 3D Multi-Body Orthodontic Models by Using Independent Imaging Sensors” Sensors, vol. 13, pp. 2033-2050 (2013) (Year: 2013).*

Park, C., et al. “Iterative closest-point based 3D stitching in dental computed tomography for a larger view of facial anatomy” Medical Imaging 2019: Physics of Medical Imaging (2019) (Year: 2019).*

Chung, M., et al. “Automatic Registration Between Dental Cone-Beam CT and Scanned Surface via Deep Pose Regression Neural Networks and Clustered Similarities” IEEE Transactions on Medical Imaging, vol. 39, No. 12 (Jul. 2020) (Year: 2020).*

Ezhov et al.; Coarse-to-fine volumetric segmentation of teeth in cone-beam ct; IEEE 16th International Symposium on Biomedical Imaging (ISBI 2019); pp. 52-56; Apr. 2019.

Macho et al.; Segmenting teeth from volumetric CT data with a hierarchical CNN-based approach; EG UK Computer Graphics and Visual Computing; pp. 109-113; Sep. 2018.

* cited by examiner

Figure 1C:
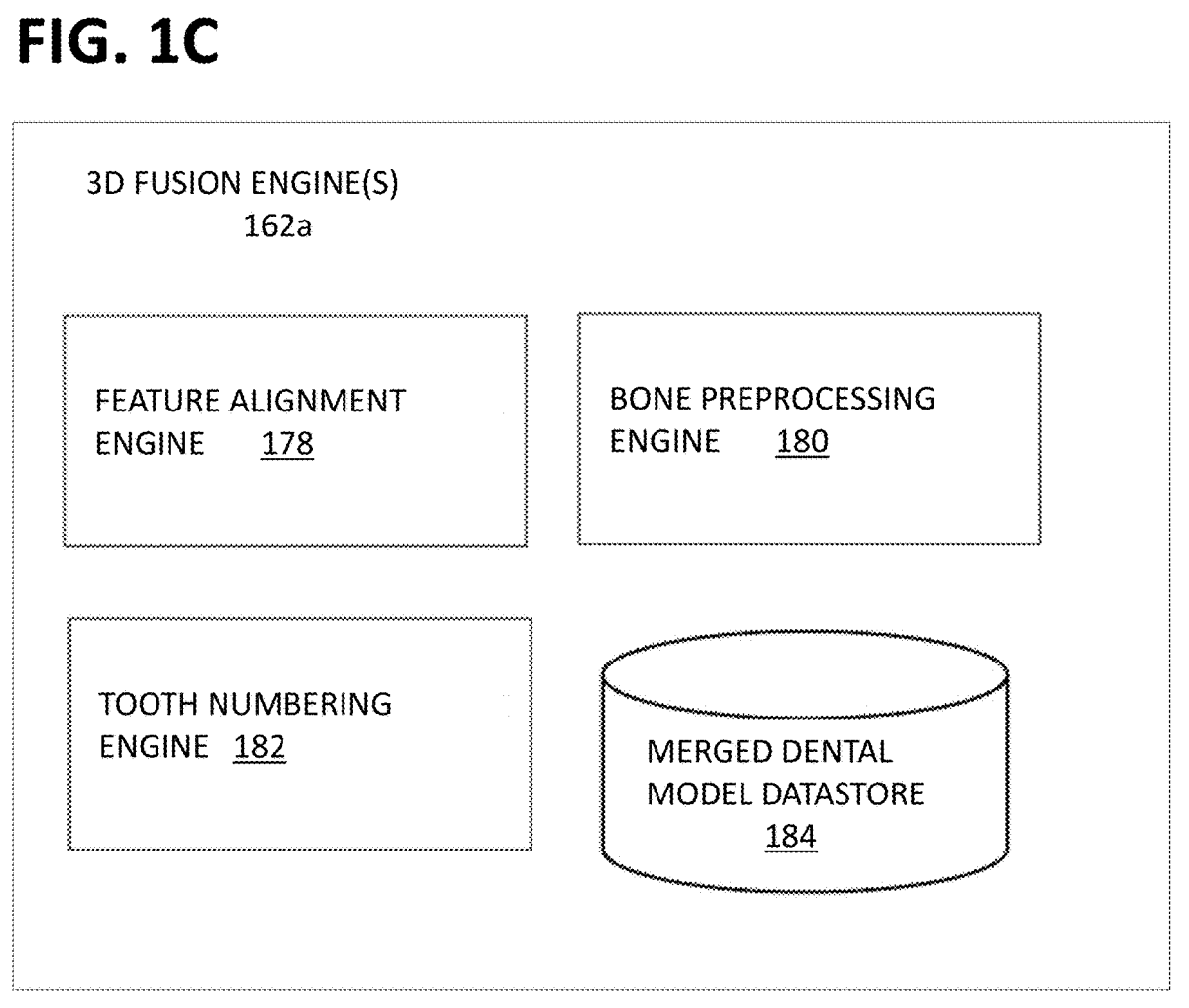

3D FUSION ENGINE(S) 162a

FEATURE ALIGNMENT ENGINE 178

BONE PREPROCESSING ENGINE 180

TOOTH NUMBERING ENGINE 182

MERGED DENTAL MODEL DATASTORE 184

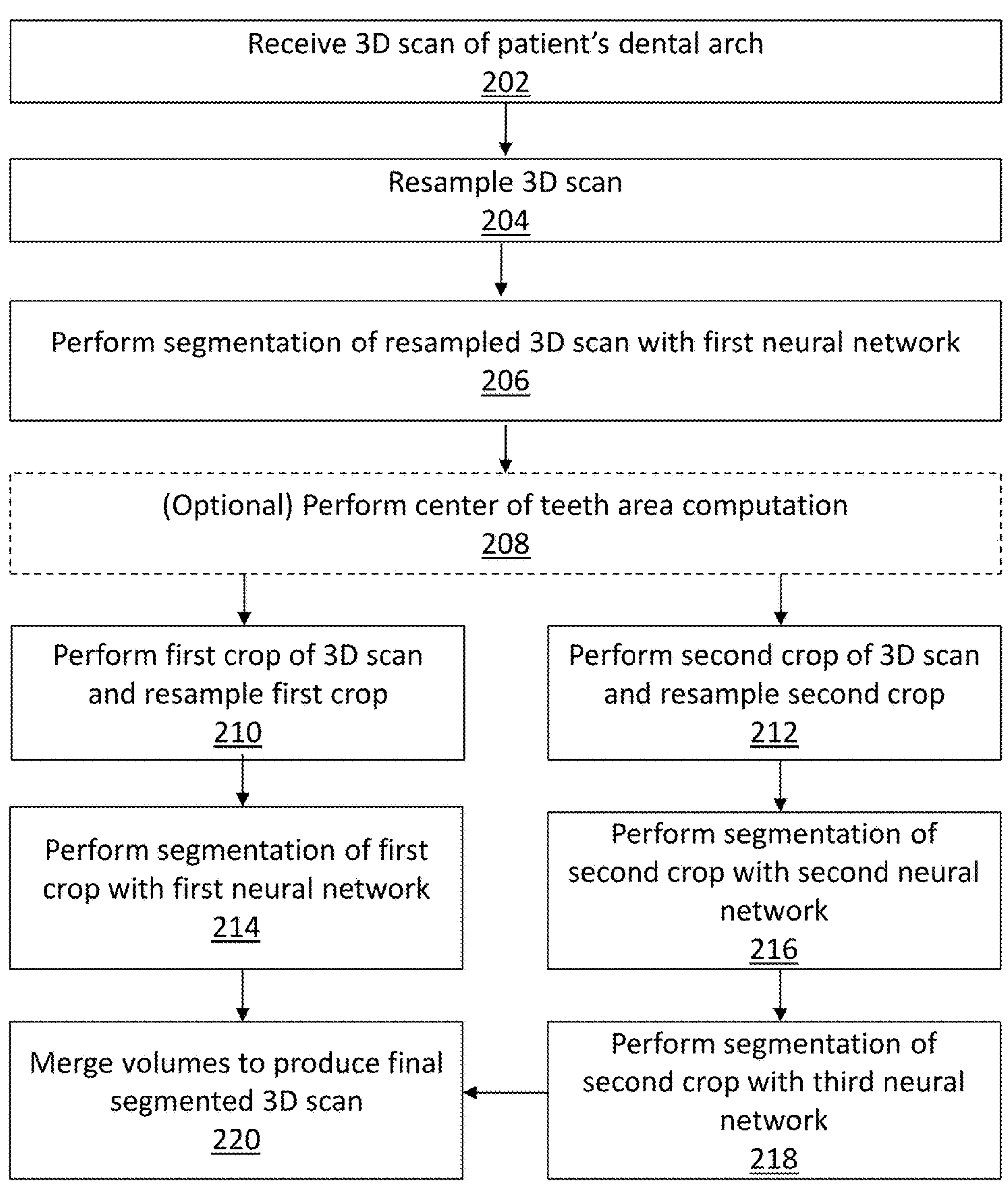
FIG. 2
Receive 3D scan of patient's dental arch
202
Resample 3D scan
204
Perform segmentation of resampled 3D scan with first neural network
206
(Optional) Perform center of teeth area computation
208
Perform first crop of 3D scan and resample first crop
210
Perform second crop of 3D scan and resample second crop
212
Perform segmentation of first crop with first neural network
214
Perform segmentation of second crop with second neural network
216
Merge volumes to produce final segmented 3D scan
220
Perform segmentation of second crop with third neural network
218

SYSTEMS AND METHODS FOR SEGMENTING DENTAL SCANS

CLAIM OF PRIORITY

This application claims priority to U.S. Provisional Patent Application No. 63/117,426, filed Nov. 23, 2020, titled "AUTOMATIC SEGMENTATION OF DENTAL CBCT SCANS," which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner and/or by the patients themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, a patient may be provided plurality of orthodontic aligners over the course of treatment to make incremental position adjustments to the patient's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Many digital scan technologies use automated tooth segmentation systems (e.g., automated systems that identify and/or number individual teeth and/or dental features in a dental model). Many of these automated tooth segmentation systems still require significant input from a technician to correctly segment the teeth. To date, there has been a great deal of work performed on 2D semantic segmentation (i.e., the segmentation of images into specific, labeled components). There has been significantly less work in 3D due to the enormous memory requirements (e.g., a medium-resolution image might contain 512×512 pixels, so to achieve the same resolution in voxels a system may require more than 256 times that amount of memory. It would be particularly helpful to provide one or more tools that may aid in segmenting, analyzing, and/or guiding treatments that may automatically and accurately segment teeth, particularly 3D datasets such as those provided from CT, CBCT, or MRI scanners.

SUMMARY OF THE DISCLOSURE

Implementations address the need to provide an automated tooth segmentation system to automatically, effectively, and accurately segment individual teeth and dental features from a 3D scan or 3D dataset of a patient's detention, with a high degree of accuracy. The present application addresses these and other technical problems by providing technical solutions and/or automated agents that automatically segment teeth and dental features using machine learning neural networks. In some implementations, segmentation of 3D datasets is performed with a set of 3D convolutional neural networks that processes different areas of the 3D dataset with different volumetric resolutions. Automatic tooth segmentation may provide the basis for implementation of automated orthodontic treatment plans, design and/or manufacture of orthodontic aligners (including series of polymeric orthodontic aligners that provide forces to correct malocclusions in patients' teeth). These apparatuses and/or methods may provide or modify a treatment plan, including an orthodontic treatment plan. The apparatuses and/or methods described herein may provide instructions to generate and/or may generate a set or series of aligners, and/or orthodontic treatment plans. The apparatuses and/or methods described herein may provide a visual representation of the patient's teeth.

In general, example apparatuses (e.g., devices, systems, etc.) and/or methods described herein may acquire a representation of a patient's teeth. The representation may be a 3D model, a 3D scan, or a 3D dataset of the patient's teeth (e.g., a 3D tooth point cloud, a 3D mesh, a CT scan, a CBCT scan, or an MRI scan). In some implementations, one or more subsets of the 3D dataset at one or more different resolutions can be used as the input.

In general, example apparatuses (e.g., devices, systems, etc.) and/or methods described herein may train a machine learning model or use a trained machine learning model to segment a 3D scan or 3D dataset of the patient's teeth. Examples of machine learning systems that may be used include, but are not limited to, Convolutional Neural Networks (CNN) such as V-Net, U-Net, ResNeXt, Xception, RefineNet, Kd-Net, SO Net, Point Net, or Point CNN, and additional machine learning systems such as Decision Tree, Random Forest, Logistic Regression, Support Vector Machine, AdaBoosT, K-Nearest Neighbor (KNN), Quadratic Discriminant Analysis, Neural Network, etc. Once the machine learning systems have been trained, they can be used to generate a segmented model of the patient's detention.

Any of the apparatuses and/or methods described herein may be part of a distal tooth scanning apparatus or method or may be configured to work with a digital scanning apparatus or method.

For example, described herein are methods that may include: receiving, in a computing device, scan data comprising a root scan (e.g., cone beam computed tomography, CT scan, MRI scan, etc.) of a patient's dentition, wherein the scan data is segmented into individual teeth; performing a coarse alignment of the scan data to a digital model of the patient's dentition using crown information to form coarsely aligned scan data, wherein the digital model of the patient's dentition includes one or more stages of a treatment plan for modifying the patient's dentition; performing a fine alignment of the coarsely aligned scan data using a 3D matching algorithm to form an aligned scan data; processing the aligned scanned data to patch teeth sockets from the aligned scan data; modify the digital model of the patient's dentition to include tooth roots from the processed aligned scan data to form a modified digital model; and display or modify the treatment plan using the modified digital model.

These methods may be methods of reviewing and/or modifying a treatment plan. In particular, these methods may allow the treatment plan to be viewed more clearly and accurately. Any of these methods may include segmenting the scan data; for example, automatically segmenting the scan data with one or more convolutional neural networks.

Any of these methods may include generating a raw aligned scan data after performing the fine alignment by modifying the digital model of the patient's dentition to include tooth roots from the scan data prior to processing the aligned scanned data; these methods may include displaying the raw aligned scan data for a user to review and correct the modified digital model.

The coarse alignment may include using a mass center of each crown of the scan data with an alignment algorithm. Alternatively, coarse alignment may include using a crown tip of each crown of the scan data with an alignment algorithm. Any of these methods may include performing fine alignment comprises applying an Iterative Closest Point (ICP), 3D matching algorithm.

In any of these methods, processing the aligned scanned data may include smoothing the aligned scan data. Processing the aligned scanned data to patch teeth sockets from the aligned scan data may include removing tooth sockets so that semitransparent representations of bone may be displayed over planned tooth movement without visual interference of moving root contours and unmovable socket contours.

Also described herein are systems for performing any of these methods, including non-transitory computer-readable storage medium storing a set of instructions capable of (e.g., configured to) perform any of these methods.

Also described herein are methods of segmenting a three-dimensional (3D) scan of a patient's dentition, the method comprising the steps of: receiving, in a computing device, a three-dimensional (3D) scan of a patient's dentition; automatically segmenting the 3D scan with one or more convolutional neural networks; incorporating the segmented 3D scan into a 3D dental model of a virtual treatment plan; and outputting the virtual treatment plan.

Any of these methods may include identifying individual segmented teeth in the virtual treatment plan; identifying a generic tooth model corresponding to the individual segmented teeth; and replacing the individual segmented teeth in the virtual treatment plan with the generic tooth model corresponding to each individual segmented tooth.

In some cases these methods may include automatically renumbering the 3D dental model of the virtual treatment plan with a watershed algorithm. Automatically segmenting the 3D scan may further comprise: downsampling the 3D scan to a lower resolution than the 3D scan; segmenting the downsampled 3D scan with a first neural network to identify the patient's teeth, the patient's upper jaw bones, and the patient's lower jaw bones; performing a center of teeth area computation to determine where the patient's teeth are positioned within the 3D scan; performing a first crop of the 3D scan; segmenting the first crop with the first neural network to produce a first volume; performing a second crop of the 3D scan; segmenting the second crop with a second neural network to produce a second volume; segmenting the second crop with a third neural network to produce a third volume; and merging the first volume, the second volume, and the third volume to produce a final segmented 3D scan.

Incorporating the segmented 3D scan into a 3D dental model of a virtual treatment plan may include: receiving the segmented 3D scan data and a virtual treatment plan; performing a coarse alignment of the segmented 3D scan with the virtual treatment plan; performing a fine alignment of the segmented 3D scan with the virtual treatment plan; stitching teeth crowns from the virtual treatment plan to corresponding teeth roots from the segmented 3D scan data; numbering individual segmented teeth in the virtual treatment plan.

Replacing the individual segmented teeth may include: determining apex positions of a selected tooth in the segmented 3D scan; moving apex positions of a generic tooth model to the apex positions of the tooth in the segmented 3D scan; overlaying contours of the generic tooth model on the tooth in the segmented 3D scan; identifying one or more discrepancies between the segmented 3D scan and the contours of the generic tooth model; computing 3D coordinates of one or more points at the one or more discrepancies between the segmented 3D scan and the generic tooth model; adding one or more 3D control points at the computed coordinates to the generic tooth model; and transforming the generic tooth model with the one or more 3D control points.

Also described herein are methods of segmenting a 3D scan of a patient's dentition, including the patient's teeth, the method comprising the steps of: receiving, in a computing device, a three-dimensional (3D) scan of the patient's dentition; downsampling the 3D scan to a lower resolution than the 3D scan; segmenting the downsampled 3D scan with a first neural network to identify the patient's teeth, the patient's upper jaw bones, and the patient's lower jaw bones; performing a center of teeth area computation to determine where the patient's teeth are positioned within the 3D scan; performing a first crop of the 3D scan; segmenting the first crop with the first neural network to produce a first volume; performing a second crop of the 3D scan; segmenting the second crop with a second neural network to produce a second volume; segmenting the second crop with a third neural network to produce a third volume; merging the first volume, the second volume, and the third volume to produce a final segmented 3D scan.

In general, the 3D scan may comprise a CT scan of the patient's dentition. The 3D scan may comprises a CBCT scan of the patient's dentition. The 3D scan may comprise an MRI scan of the patient's dentition.

The first and second neural networks may comprise V-net neural networks. In some examples, the first crop has a lower resolution than the second crop. The downsampled 3D scan, the first crop, and the second crop may have a data input dimension no larger than 256×256×256. The first crop may encompass scan data related to the patient's upper jaw bones or lower jaw bones. The second crop may encompass scan data related to the patient's teeth.

The first volume may comprise an upper bone, lower bone, and binary teeth segmentation. The second volume may comprise an upper bone, lower bone, and binary teeth segmentation. The third volume may comprise a multi-class teeth segmentation.

Also described herein are methods of adding segmented 3D scan data to a virtual treatment plan. For example, a method may include: receiving segmented 3D scan data and a virtual treatment plan; performing a coarse alignment of the segmented 3D scan with the virtual treatment plan; performing a fine alignment of the segmented 3D scan with the virtual treatment plan; stitching teeth crowns from the virtual treatment plan to corresponding teeth roots from the segmented 3D scan data; numbering individual segmented teeth in the virtual treatment plan.

Any of these methods may include preprocessing bone segments to patch sockets or missing data in the virtual treatment plan.

Also described herein are methods of adjusting a generic tooth model to better fit into a segmented tooth from a 3D scan. For example, a method may include: determining apex positions of a selected tooth in a segmented 3D scan; moving apex positions of a generic tooth model to the apex positions of the tooth in the segmented 3D scan; overlaying contours of the generic tooth model on the tooth in the segmented 3D scan; identifying one or more discrepancies between the segmented 3D scan and the contours of the generic tooth model; computing 3D coordinates of one or more points at the one or more discrepancies between the segmented 3D scan and the generic tooth model; adding one or more 3D control points at the computed coordinates to the generic tooth model; and transforming the generic tooth model with the one or more 3D control points.

Systems, including dental treatment systems are also provided herein, and can comprise systems with: one or more processors; memory coupled to the one or more processors, the memory configured to store computer-program instructions that, when executed by the processor, cause the processor to execute a computer-implemented method, the computer-implemented method comprising: receiving, in a computing device, scan data comprising a bone root scan of a patient's dentition, wherein the scan data is segmented into individual teeth; performing a coarse alignment of the scan data to a digital model of the patient's dentition using crown information to form coarsely aligned scan data, wherein the digital model of the patient's dentition includes one or more stages of a treatment plan for modifying the patient's dentition; performing a fine alignment of the coarsely aligned scan data using a 3D matching algorithm to form an aligned scan data; processing the aligned scanned data to patch teeth sockets from the aligned scan data; modifying the digital model of the patient's dentition to include tooth roots from the processed aligned scan data to form a modified digital model; and displaying or modifying the treatment plan using the modified digital model.

Other systems, including dental treatment systems are also provided herein, and can comprise systems with: one or more processors; memory coupled to the one or more processors, the memory configured to store computer-program instructions that, when executed by the processor, cause the processor to execute a computer-implemented method, the computer-implemented method comprising: receiving, in the dental treatment system, a three-dimensional (3D) scan of a patient's dentition; automatically segmenting the 3D scan with one or more convolutional neural networks; incorporating the segmented 3D scan into a 3D dental model of a virtual treatment plan; and outputting the virtual treatment plan.

In another example, a system, such as a dental treatment system, can comprise: one or more processors; memory coupled to the one or more processors, the memory configured to store computer-program instructions that, when executed by the processor, cause the processor to execute a computer-implemented method, the computer-implemented method comprising: receiving, in the dental treatment system, a three-dimensional (3D) scan of the patient's dentition; downsampling the 3D scan to a lower resolution than the 3D scan; segmenting the downsampled 3D scan with a first neural network to identify the patient's teeth, the patient's upper jaw bones, and the patient's lower jaw bones; performing a center of teeth area computation to determine where the patient's teeth are positioned within the 3D scan; performing a first crop of the 3D scan; segmenting the first crop with the first neural network to produce a first volume; performing a second crop of the 3D scan; segmenting the second crop with a second neural network to produce a second volume; segmenting the second crop with a third neural network to produce a third volume; merging the first volume, the second volume, and the third volume to produce a final segmented 3D scan.

Another system is provided, such as a dental treatment system, that comprises: one or more processors; memory coupled to the one or more processors, the memory configured to store computer-program instructions that, when executed by the processor, cause the processor to execute a computer-implemented method, the computer-implemented method comprising: receiving segmented 3D scan data and a virtual treatment plan; performing a coarse alignment of the segmented 3D scan with the virtual treatment plan; performing a fine alignment of the segmented 3D scan with the virtual treatment plan; stitching teeth crowns from the virtual treatment plan to corresponding teeth roots from the segmented 3D scan data; and numbering individual segmented teeth in the virtual treatment plan.

A dental treatment system is also provided, comprising: one or more processors; memory coupled to the one or more processors, the memory configured to store computer-program instructions that, when executed by the processor, cause the processor to execute a computer-implemented method, the computer-implemented method comprising: determining apex positions of a selected tooth in a segmented 3D scan; moving apex positions of a generic tooth model to the apex positions of the tooth in the segmented 3D scan; overlaying contours of the generic tooth model on the tooth in the segmented 3D scan; identifying one or more discrepancies between the segmented 3D scan and the contours of the generic tooth model; computing 3D coordinates of one or more points at the one or more discrepancies between the segmented 3D scan and the generic tooth model; adding one or more 3D control points at the computed coordinates to the generic tooth model; and transforming the generic tooth model with the one or more 3D control points.

All of the methods and apparatuses described herein, in any combination, are herein contemplated and can be used to achieve the benefits as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Figure 1A:
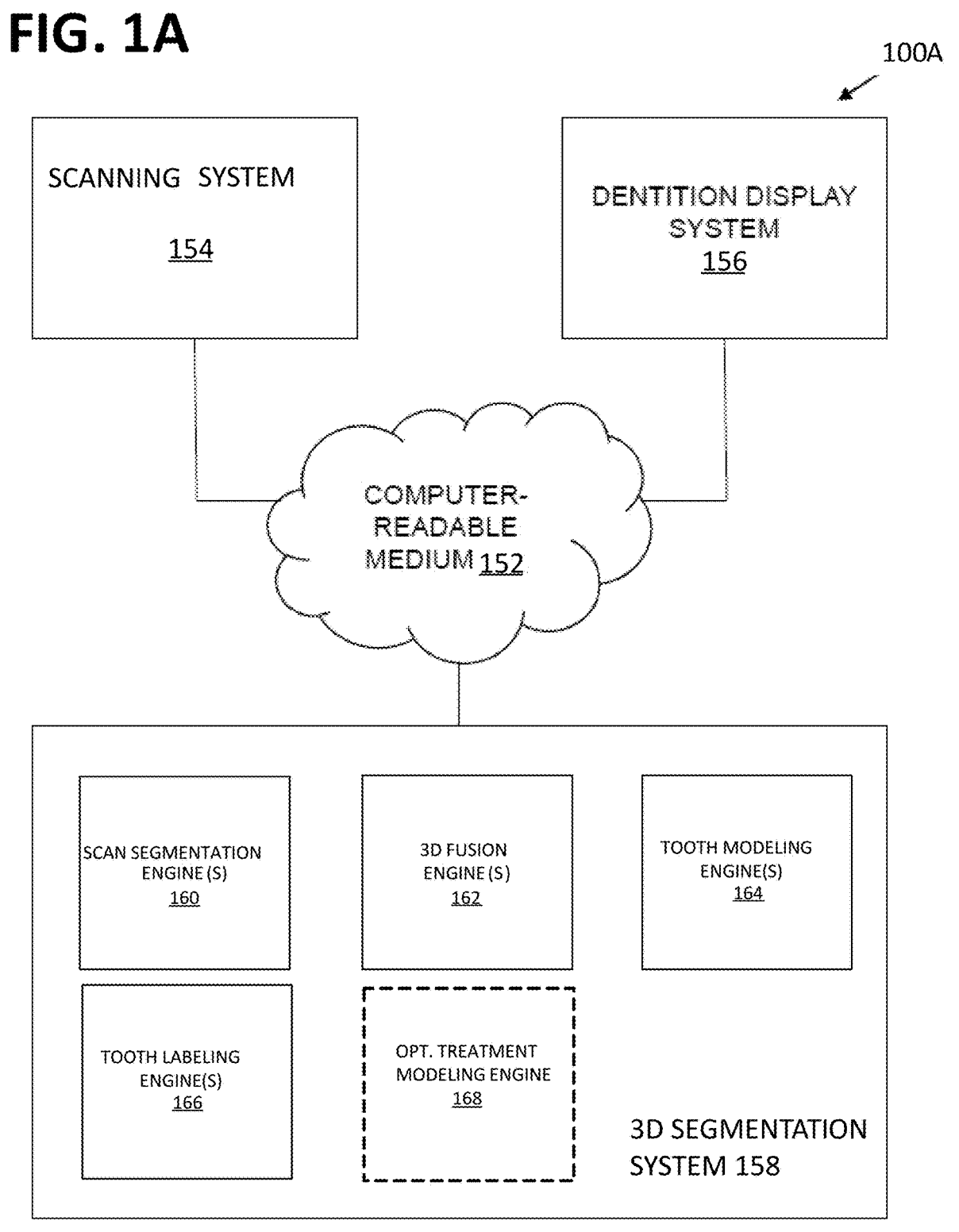
Figure 1B:
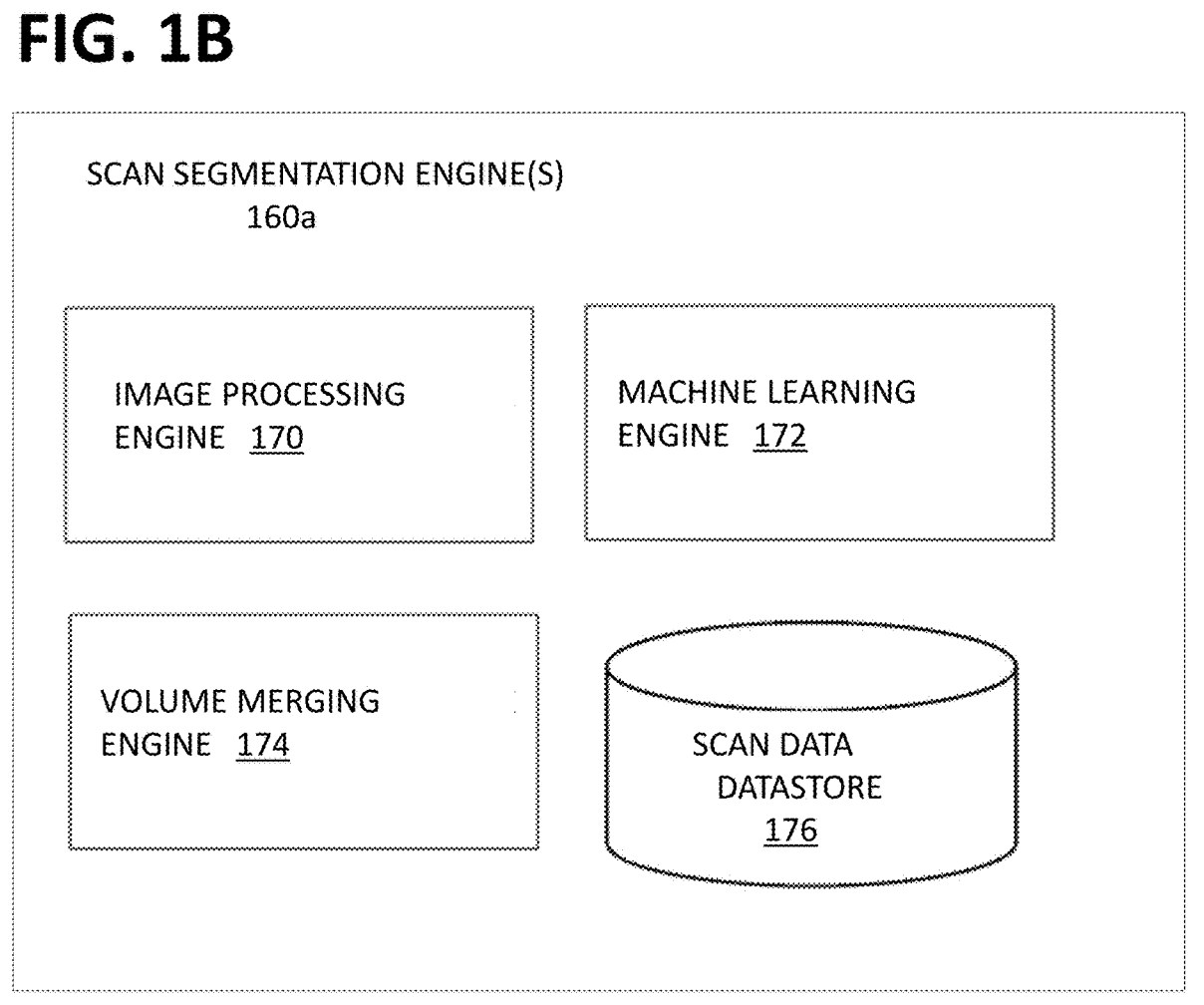

FIG. 1A is a diagram showing an example of a computing environment configured to digitally scan a dental arch and determine a post-treatment tooth position score.

FIG. 1B is a diagram showing an example of scan segmentation engine(s).

FIG. 1C is a diagram showing an example of 3D fusion engine(s).

FIG. 2 illustrates one example of a method for segmenting a 3D scan of a patient's teeth, such as a CT scan, a CBCT scan, or a MRI scan

DETAILED DESCRIPTION

Figure 1D:
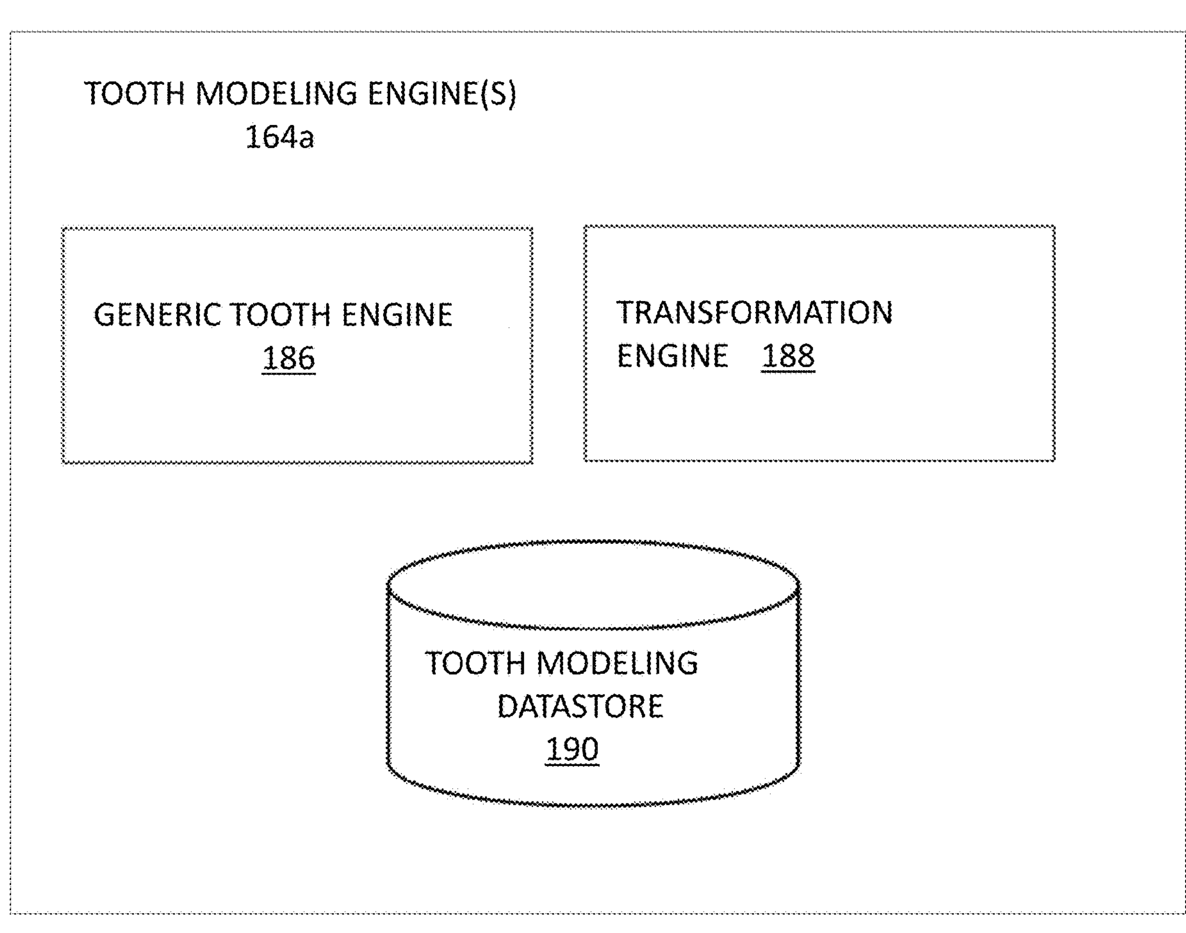
FIG. 1D is a diagram showing an example of a tooth modeling engine(s).

Described herein are apparatuses (e.g., systems, computing device readable media, devices, etc.) and methods for training a machine learning model to recognize "segmentation elements" corresponding to segmentation of patient's dentition. One object of the present disclosure is to use machine learning technology to provide an automatic segmentation system that can segment a 3D model of a patient's detention into individual teeth and dental features. The machine learning model can make this determination based upon data including patient demographics, tooth measurements, tooth surface mesh, processed tooth features, and historical patient data. These methods and apparatus can use this information to train a machine learning model and use the machine learning model to segment the patient's detention.

For example, described herein are apparatuses and/or methods, e.g., systems, including systems to automatically implement processes that incorporate a tooth segmentation system. When the system is triggered by a request for dental segmentation, the system can retrieve a 3D scan or 3D dataset representing a patient's dentition, and process different areas of the 3D scan or 3D dataset with different volumetric resolutions to output a high-performance final segmentation. In some examples, the different areas of the scan can be passed into a machine learning model, which may use machine learning technology (e.g., Convolutional Neural Network (CNN), Decision Tree, Random Forest, Logistic Regression, Support Vector Machine, AdaBOOST, K-Nearest Neighbor (KNN), Quadratic Discriminant Analysis, Neural Network, etc.) to return a segmented model of the patient's detention. The results may be provided on demand and/or may be stored in a memory (e.g., database) for later use.

The apparatuses and/or methods described herein may be useful in planning and fabrication of dental appliances, including elastic polymeric positioning appliances, is described in detail in U.S. Pat. No. 5,975,893, and in published PCT application publication No. WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives orthodontic treatment, including orthodontic treatment with a series of orthodontic aligners.

The apparatuses and/or methods (e.g., systems, devices, etc.) described below can be used with and/or integrated into an orthodontic treatment plan. The apparatuses and/or methods described herein may be used to segment a patient's teeth from a three-dimensional model, such as a 3D mesh model, a 3D point cloud, or a 3D scan (e.g., CT scan, CBCT scan, MRI scan, etc.), and this segmentation information may be used to simulate, modify and/or choose between various orthodontic treatment plans. Segmenting the patient's teeth can be done automatically (e.g., using a computing device). For example, segmentation can be performed by a computing system automatically by evaluating data (such as three-dimensional scan, or a dental impression) of the patient's teeth or arch.

As described herein, an intraoral scanner may image a patient's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The three-dimensional scan can generate a 3D mesh model, or a 3D point cloud model representing the patient's arch, including the patient's teeth and gums. Further computer processing as described herein can segment or separate the 3D mesh or 3D point cloud into individual teeth and gums.

In other implementations, the 3D scan can also be a CT scan, a CBCT scan, a MRI scan, or any other 3D medical scan. The automated systems described herein can provide a segmented model of the patient's dentition directly from the 3D scan.

An automated tooth segmentation system, as used herein, may include a system that uses automated agents to identify and/or number individual teeth and/or dental features of virtual representations of teeth, such as teeth represented in a three-dimensional scan, 3D dental mesh model, or 3D point cloud resulting from a digital scan. The present disclosure presents one or more novel processes for identifying and segmenting a patient's teeth during a segmentation process. Some implementations herein may solve technical problems related to optimizing and/or increasing the accuracy and efficiency of digital dental scanning technologies.

FIG. 1A is a diagram showing an example of a computing environment 100A configured to facilitate gathering and processing digital scans of a dental arch with teeth and/or bones therein. The environment 100A includes a computer-readable medium 152, a scanning system 154, a dentition display system 156, and a 3D segmentation system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a patient's dental arch. A "dental arch," as used herein, may include at least a portion of a patient's dentition formed by the patient's maxillary and/or mandibular teeth, when viewed from an occlusal perspective. A dental arch may include one or more maxillary or mandibular teeth of a patient, such as all teeth on the maxilla or mandible or a patient. The scanning system 154 may include memory, one or more processors, and/or sensors to detect contours on a patient's dental arch. The scanning system 154 may be implemented as a camera, an intraoral scanner, an x-ray device, an infrared device, a medical scanning device (e.g., CT scanner, CBCT scanner, MRI scanner) etc. In some implementations, the scanning system 154 is configured to produce 3D scans of the patient's dentition. In other implementations the scanning system 154 is configured to produce 2D scans or images of the patient's dentition. The scanning system 154 may include a system configured to provide a virtual representation of a physical mold of patient's dental arch. The scanning system 154 may be used as part of an orthodontic treatment plan. In some implementations, the scanning system 154 is configured to capture a patient's dental arch at a beginning stage, an intermediate stage, etc. of an orthodontic treatment plan. The scanning system 154 may be further configured to receive 2D or 3D scan data taken previously or by another system.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The 3D segmentation system 158 may include a computer system, including memory and one or more processors, configured to process scan data from the scanning system 154. In some examples, the 2D or 3D scan data can be segmented into individual dental components and processed into a 3D model of the patient's teeth. The 3D segmentation system can be configured to input one or more different areas of the 2D scan, 3D scan, or 3D model into a machine learning model to automatically segment the scan or model into individual dental components, including segmenting the scan or model into individual teeth, bones, interproximal spaces between teeth, and/or gingiva. The segmented 2D/3D scan or model can be used to create an implement a dental treatment plan for the patient. For example, a digital treatment planning software may incorporate the 3D segmentation system and receive a 3D scan of the patient's dentition. The 3D segmentation system may then be configured to automatically segment the 3D scan. The digital treatment planning software may then be configured to automatically generate a dental treatment plan for the patient, which may further include generating a 3D model of the patient's dentition that includes the 3D segmentation. The 3D segmentation system 158 may include scan segmentation engine(s) 160, 3D fusion engine(s) 162, tooth modeling engine(s) 164, tooth labeling engine(s) 166, and optional treatment modeling engine(s) 168. One or more of the modules of the 3D segmentation system 158 may be coupled to each other or to modules not shown.

The scan segmentation engine(s) 160 of the 3D segmentation system 158 may implement automated agents to process 2D or 3D scans taken by the scanning system 154. In some implementations, the scan segmentation engine(s) 160 formats scan data from a scan of a dental arch into one or more partitions, volumes, crops, or areas of the scan. The scan segmentation engine(s) may be integrated into a digital treatment planning software. The one or more partitions, volumes, crops, or areas of the scan can be a subset or section of the original scan. In some implementations, the one or more partitions, volumes, crops, or areas of the scan can have a resolution different than the resolution of the original 2D or 3D scan. For example, the one or more partitions, volumes, crops, or areas of the scan can have a lower resolution than the original scan. In other implementations, the one or more partitions, volumes, crops, or areas of the scan can have the same resolution of the original scan. The scan segmentation engine(s) 160 can be further configured to implement automated agents to segment the 2D or 3D scan. In one implementation, the scan segmentation engine(s) can input the or more partitions, volumes crops, or areas of the scan into one or more machine learning models for segmentation into individual dental features such as upper bone, lower bone, and binary teeth segmentation. For lower bone/upper bone/binary teeth segmentation, every voxel belonging to the teeth is labeled by the system with a value '1', every voxel belonging to lower bone is labeled by the system with a value '2', every voxel belonging to upper bone is labeled with a value '3', and all other voxels are labeled with a value '0'. The segmentations of the one or more partitions, volumes, crops, or areas of the scan can be merged to generate full semantic segmentation of the 2D or 3D scan.

The 3D fusion engine(s) 162 of the 3D segmentation system 158 can implement automated agents to align segmented scan data from the scan segmentation engine(s) 160 with a digital dental 3D treatment plan of the patient. The 3D fusion engine(s) may be integrated into a digital treatment planning software. In some implementations, the 3D fusion engine(s) 162 provides coarse alignment of segmented scan data and triangulation of each labeled volume with corresponding dental features of the digital dental 3D treatment plan. The 3D fusion engine(s) 162 can then provide fine alignment of the segmented scan data with the dental treatment plan. In some implementations, the 3D fusion engine can preprocess the aligned segmented scan data and digital treatment plan for reduction of digital noise and suppression of potential segmentation errors. The 3D fusion engine can be further configured to accurately number individual teeth in the digital treatment plan. Additionally, the 3D fusion engine can implement automated agents to stich scan data representing tooth crows to digital treatment plan data representing tooth roots, providing the best possible resolution in the final segmented digital treatment plan.

The tooth modeling engine(s) 164 may implement automated agents to replace or modify low-quality or low-resolution segmentation data from the 2D/3D scan with higher quality generic tooth models. The tooth modeling engine(s) may be integrated into a digital treatment planning software. In one implementation, the tooth modeling engine(s) 164 may be configured to identify a segmented tooth from the segmented scan data and identify a generic tooth model corresponding to the segmented tooth. In one implementation, the tooth modeling engine(s) 164 may implement automated agents to fit the generic tooth model into the segmented tooth. The generic tooth model can be modified/adjusted/rotated to precisely fit within the segmented tooth. The tooth modeling engine(s) 164 may then be configured to implement automated agents to transform the adjusted generic tooth model into the digital treatment plan for the patient. This process can be repeated for all the segmented teeth from the 2D/3D scan.

The tooth labeling engine(s) 166 may implement automated agents to label segmented teeth of segmented 2D/3D scan from the scan segmentation engine(s) 160. The tooth labeling engine(s) may be integrated into a digital treatment planning software. In one implementation, the tooth labeling engine receives the 2D/3D segmented scan. The tooth labeling engine can apply a morphological erosion algorithm to the segmented scan to divide the segmented scan into N voxel volumes, where N is the number of teeth in the segmented scan. In one implementation, any volumes smaller than a first threshold can be removed from the erosion process to remove noise and artifacts from the volume. The tooth labeling engine(s) 166 may further be configured to "seed" the segmented 2D/3D scan with seeds that reflect the teeth morphology (e.g., with shapes that reflect the curvature and rotation of the teeth). An erosion algorithm can then be applied to the seeded scan to produce a label map with segmented teeth.

The optional treatment modeling engine(s) 168 may be configured to use the segmented 3D model, segmented scan, and/or the combination of the segmented scan and the digital dental model to store and/or provide instructions to implement orthodontic treatment plans and/or the results of orthodontic treatment plans. The treatment modeling engine(s) may be integrated into a digital treatment planning software. The optional treatment modeling engine(s) 168 may provide the results of orthodontic treatment plans on a 3D model. In some embodiments, the 3D model can be rendered into one or more 2D image(s) from a plurality of viewing angles. The optional treatment modeling engine(s) 168 may model the results of application of orthodontic aligners to the patient's dental arch over the course of an orthodontic treatment plan. In some embodiments, the treatment modeling engine(s) can be configured to save, transmit, or output the digital dental model and/or a digital orthodontic treatment plan. In some embodiments, the digital dental model and/or a digital orthodontic treatment plan can be displayed on a display for a user of the digital treatment planning software, such as a physician. The user can edit or make changes to the proposed digital dental model and/or a digital orthodontic treatment plan, such as by interacting with a user input device (e.g., mouse and keyboard, touchscreen, joystick, etc.) of the digital treatment planning software.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein. In some examples, the engines discussed herein can be implemented in a digital orthodontic treatment planning software.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

FIG. 1B is a diagram showing an example of the scan segmentation engine(s) 160*a*. The scan segmentation engine(s) 160*a* may include an image processing engine 170, a machine learning engine 172, a volume merging engine 174, and a scan data datastore 176. One or more of the modules of the scan segmentation engine(s) 160*a* may be coupled to each other or to modules not shown.

The image processing engine 170 may implement one or more automated agents configured to format 2D or 3D scan data from a scan of a dental arch scan data into one or more partitions, volumes, crops, or areas of the scan. For example, the image processing engine may receive or access a 3D scan of a patient's dentition, such as a CT scan, a CBCT scan, or a MRI scan, which can include high-resolution imaging data of the patient's dental features, including the patient's teeth and the upper and lower bones of the patient's jaw. The image processing engine can then process the scan into one or more partitions, volumes, crops, or areas of the scan which may be a subset of the original scan. For example, the one or more partitions, volumes, crops, or areas of the scan can be, for example, a crop with data only representing the upper bone of the jaw, the lower bone of the jaw, and/or the teeth of the patient. In one implementation, the image processing engine can take into account specific geometric features of the 2D/3D scan to determine how/where to crop the scan. For example, the image processing engine can implement a center of teeth area computation to determine where the patient's teeth are located in the 2D/3D scan. In one specific implementation, the center of teeth can be computed as a geometric center of all teeth in 3D space using a binary teeth segmentation in which every voxel belonging to teeth is labeled with a value '1' and all other voxels are labeled with a value '0'. Using the formula:

$$C = \frac{x_1 + x_2 + \cdots + x_k}{k}$$

Where k is a number of 'teeth' voxels in the segmented volume and $x_1, x_2, \ldots, x_k$ are 'teeth' voxels in 3D space. This calculation gives a center of teeth areas estimation, which can then be used by the system to generate one or more partitions, volumes, crops, or areas of the scan that include scan data of the patient's teeth. The image processing engine 170 may be further configured to implement automated agents to resample or adjust the resolution of the 2D/3D scan or of the one or more partitions, volumes, crops, or areas of the scan. For example, in one implementation, the entire 2D/3D scan may be resampled to have a lower resolution than the native resolution of the scan. In another implementation, one or more partitions, volumes, crops, or areas of the scan may be resampled to have a different (e.g., lower) resolution. The image processing engine 170 may provide the processed scan data and/or other data to the scan data datastore 176.

The machine learning engine 172 may implement one or more automated agents configured to apply one or more machine learning engines to segment the processed scan data from the image processing engine. For example, the machine learning engine 172 can use, as an input, the original 2D/3D scan (e.g., a CT scan, CBCT scan, or MRI scan) and/or the one or more partitions, volumes, crops, or areas of the scan from the image processing engine. As described above, the one or more partitions, volumes, crops, or areas of the scan may also have various resolutions, as some of the crops may have a lower resolution than the original 2D/3D scan. A plurality of the aforementioned inputs may be used to generate segmentation data. For example, a low-resolution version of the 2D/3D scan may be input into the machine learning engine to generate an upper bone/lower bone/binary teeth segmentation. For lower bone/upper bone/binary teeth segmentation, every voxel belonging to the teeth is labeled by the system with a value '1', every voxel belonging to lower bone is labeled by the system with a value '2', every voxel belonging to upper bone is labeled with a value '3', and all other voxels are labeled with a value '0'. Additionally, one or more partitions, volumes, crops, or areas of the scan at different resolutions can be input into the machine learning engine to generate segmentation data. Higher resolution crops of the patient's teeth can be input into the machine learning engine to generate segmentation data of the patient's teeth. Additionally, lower resolution crops of the patient's upper/lower bones can be input into the machine learning engine to generate segmentation data. The machine learning engine 172 may provide the segmented data and/or other data to the scan data datastore 176.

Examples of machine learning systems that may be used by the machine learning engine include, but are not limited to, Convolutional Neural Networks (CNN) such as V-net, U-Net, ResNeXt, Xception, RefineNet, Kd-Net, SO Net, Point Net, or Point CNN, and additional machine learning systems such as Decision Tree, Random Forest, Logistic Regression, Support Vector Machine, AdaBoosT, K-Nearest Neighbor (KNN), Quadratic Discriminant Analysis, Neural Network, etc. Additionally, the variations of the CNNs described above can be implanted. For example, a CNN such as Unet can be modified to use alternative convolutional blocks (e.g., ResNeXt or Xception) instead of the VGG-style blocks that are implemented by default.

The volume merging engine 174 may implement one or more automated agents configured to merge the segmented data from the machine learning engine 172 into a full semantic segmentation of the 2D or 3D scan, including segmentation of the patient's upper bone/lower bone/individual teeth. As described above, the machine learning engine may provide segmentation data from various scan data inputs, including segmenting the original 2D/3D scan, segmenting a resampled (e.g., low resolution) scan, and/or segmenting one or more partitions, volumes, crops, or areas of the scan. The resulting segmentation data comprises a plurality of segmented volumes, each volume potentially having varying resolutions and pertaining to varying locations within the original 2D/3D scan. The volume merging engine 174 can be configured to implement automated agents to merge the segmented volumes from the machine learning engine into a single, comprehensive segmentation of the original 2D or 3D scan. For example, the volume merging engine 174 can be configured to merge a first volume (e.g., a low-resolution upper bone/lower bone/binary teeth segmentation volume) and a second volume (e.g., a high-resolution, multi-class teeth segmentation volume) using the following steps: 1) remove binary teeth labels from the first volume; 2) adjust the resolution of the first volume to be the same as the second volume; and 3) replace voxels in the first volume with voxels from the second volume. The resulting volume contains information about high-resolution teeth and low-resolution upper bones and lower bones.

The scan data datastore 176 may be configured to store data related to the 2D or 3D scan, the cropped or resampled scan data, the segmented scan data, and/or the merged volume data from the modules described above.

FIG. 2 illustrates one example of a method for segmenting a 3D scan of a patient's teeth, such as a CT scan, a CBCT scan, or an MRI scan. It should be understood that this method can also be employed to segment a 2D scan of a patient's teeth, or to segment a 3D model of the patient's teeth. This method may be automatically implemented by a system, such as one or more of the systems in the computing environment 100A, shown in FIG. 1A, or in a digital orthodontic treatment planning software executed on a computing system such as a PC, smartphone, or tablet. This method may also be automatically implemented in the scan segmentation engine(s) 160 of FIG. 1A, and in the scan segmentation engine(s) 160*a* of FIG. 1B.

At an operation 202, the system may automatically receive three-dimensional (3D) scan of a patient's dentition. The scan may be generated from 3D scanning machine collected directly from the patient (e.g., using an intraoral scanner, a CT scanner, a CBCT scanner, a MRI scanner) or indirectly (e.g., by scanning a mold of the patients' dentition and/or by receiving 3D scans of the patient taken by another, etc.).

At an operation 204, the system may automatically resample the 3D scan. The resampling can occur within a digital orthodontic treatment planning software. In one implementation, resampling the 3D scan can comprise reducing a resolution of the 3D scan. In one specific implementation, the data input dimension of the resampled scan can be 256×256×256 and the resolution can be lower than the original 3D scan. Generally, the scan can be resampled to a data input dimension that can be input into a machine learning model, such as a 3D neural network. Many neural networks are limited by an input data dimension of 256×256×256, however it should be understood that some neural networks may have larger input data dimension limits.

At an operation 206, the resampled 3D scan can be input into a first machine learning model, such as a neural network, to produce segmentation data from the resampled 3D scan. The first machine learning model can be implemented in a digital orthodontic treatment planning software. In one implementation, the segmentation data can include upper bone segmentation data, lower bone segmentation data, and binary teeth segmentation data. For lower bone/upper bone/binary teeth segmentation, every voxel belonging to the teeth is labeled by the system with a value '1', every voxel belonging to lower bone is labeled by the system with a value '2', every voxel belonging to upper bone is labeled with a value '3', and all other voxels are labeled with a value '0'.

Next, at an operation 208, the system may optionally perform computations to determine geometric features of the 3D scan or of the resampled 3D scan. For example, the system may perform a center of teeth area computation to determine where the teeth of the patient are located in the scan. Alternatively, computations may be performed to locate the upper/lower bones of the patient's jaw. The computations can be implemented in a digital orthodontic treatment planning software, for example.

Next, at an operation 210, the system may perform a first crop of the 3D scan. The first crop can be resampled to a resolution lower than the original 3D scan, and can have a data input dimension suitable for input into a machine learning model (e.g., 256×256×256). In one implementation, the system can use the computations from operation 208 to determine how/where to make the crops of the scan. For example, if the computations in operation 208 identify the location(s) of the upper/lower bones in the scan, the first crop in operation 210 can be a crop that encompasses the upper or lower bones of the patient.

Similarly, at an operation 212, the system may perform a second crop of the 3D scan. The second crop can be resampled to a resolution equal to or lower than the original 3D scan, but higher than the resolution of the crop in operation 210, and can have a data input dimension suitable for input into a machine learning model (e.g., 256×256×256). In one implementation, the system can use the computations from operation 208 to determine how/where to make the crops of the scan. For example, if the computations in operation 208 identify the location(s) of the teeth in the scan, the second crop in operation 212 can be a crop that encompasses the patient's teeth. In one specific implementation, it is desirable that the crop of the patient's teeth has a higher resolution than the crop(s) of the upper/lower bones of the patient. The crops can be performed by the digital orthodontic treatment planning software in some implementations.

At operation 214, the first crop can be input into the first machine learning model, such as a neural network, to produce segmentation data from the first crop. As described above, the first machine learning model can be implemented in a digital orthodontic treatment planning software. In one implementation, the first crop comprises a low resolution crop and pertains to an area of the original 3D scan that includes the upper and/or lower bones of the patient's jaw. This operation can therefore be used to generate segmentation data of the upper/lower bones of the patient's jaw.

At operation 216, the second crop can be input into a second machine learning model, such as a neural network, to produce segmentation data from the second crop. The second machine learning model can also be implemented in a digital orthodontic treatment planning software. In one implementation, the second crop comprises a high resolution crop and pertains to an area of the original 3D scan that includes the patient's teeth. This operation can therefore be used to generate segmentation data of the patient's teeth. In one implementation, the teeth segmentation can be a binary teeth segmentation.

At operation 218, the second crop can be input into a third machine learning model, such as a neural network, to produce segmentation data from the second crop. The third machine learning model can also be implemented in a digital orthodontic treatment planning software. In one implementation, the second crop comprises the same high resolution crop from operation 212, and pertains to an area of the original 3D scan that includes the patient's teeth. This operation can therefore be used to generate segmentation data of the patient's teeth. In one implementation, the teeth segmentation can be a multi-class teeth segmentation. For multi-class teeth segmentation, every voxel belonging to the dedicated tooth is labeled by the system with its tooth number value and all other voxels are labeled with a value '0' (e.g., so the system assigns labels with values 0-32).

At an operation 220, the system can merge the volumes from operations 206, 214, and 216 to produce a final segmented 3D scan of the patient. The merging operations described herein can be implemented in a digital orthodontic treatment planning software. As described above, the volume from operation 206 comprises the segmentation result from a low resolution version of the original 3D scan, and can include segmentation data on the upper/lower bones as well as a binary teeth segmentation. The volume from operation 214 can comprise a cropped and resampled version of the original 3D scan, and can be directed to areas of the 3D scan that include data on the patient's upper and/or lower bones. The volume from operation 216 can comprise a cropped and resampled version of the original scan, and can be directed to areas of the 3D scan that include data on the patient's teeth. In some implementations, the resolution of the volume from operation 216 is higher than the resolution of the volumes from operations 206 and 214. The following steps can be used to merge the volumes, including a first volume (e.g., a low-resolution upper bone/lower bone/binary teeth segmentation volume) and a second volume (e.g., a high-resolution, multi-class teeth segmentation volume): 1) remove binary teeth labels from the first volume; 2) adjust the resolution of the first volume to be the same as the second volume; and 3) replace voxels in the first volume with voxels from the second volume. The resulting volume contains information about high-resolution teeth and low-resolution upper bones and lower bones.

Figure 3A:
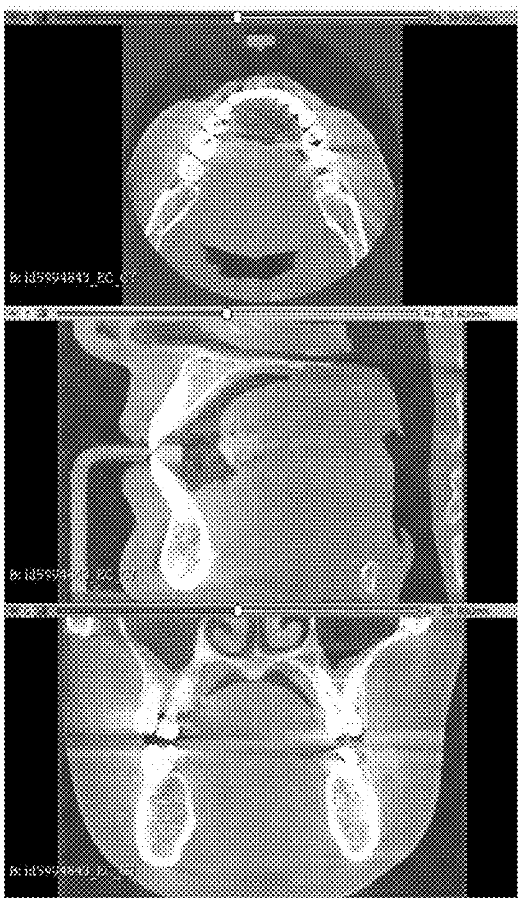
FIG. 3A-3C illustrate the results of the segmentation process described above and in FIG. 2.
Figure 3B:
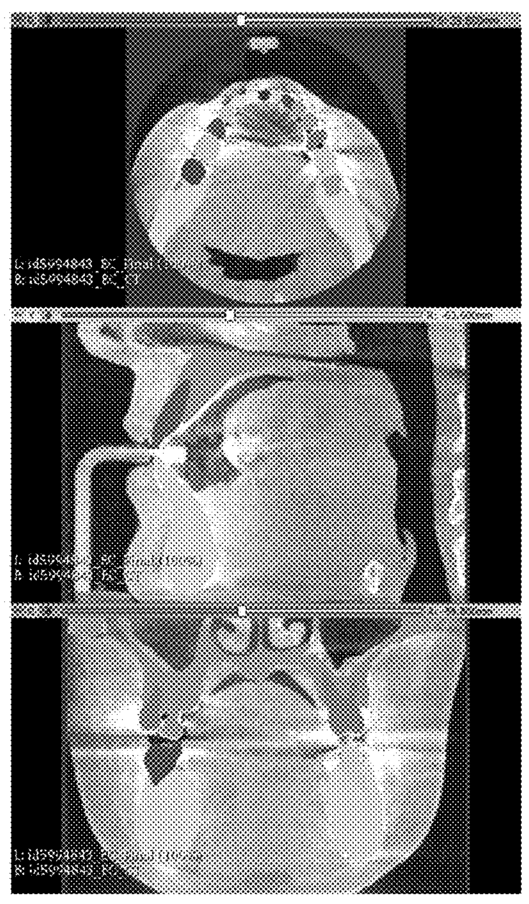
Figure 3C:
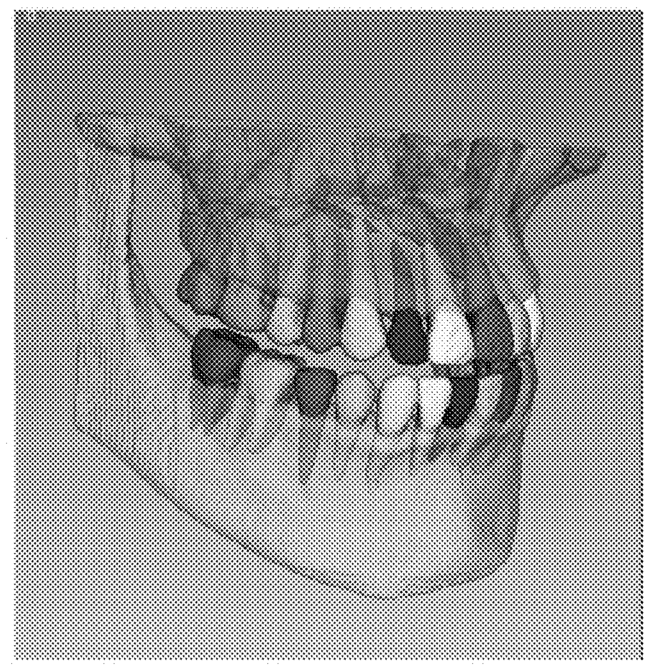

FIG. 3A-3C illustrate the results of the segmentation process described above and in FIG. 2. For example, FIG. 3A illustrates multiple views of a 3D scan of a patient's dentition, such as a CBCT scan. FIG. 3B illustrates multiple views of the 3D scan along with segmentation data representing the patient's upper/lower bones and the patient's teeth. FIG. 3C is an example of a full 3D dental model with segmented teeth and upper/lower bones as a result of the process described above. These views of the 3D scan can be received or generated by the digital orthodontic treatment planning software and presented to a user of the software, such as a physician. In some embodiments, the user can manipulate or interact with the images, including changing or rotating a perspective of the image or zooming in or out of the images. Additionally, the user can edit or change segmentation parameters of the scan and/or segmentation data, including changing, modifying, or removing segmentation data.

Figure 4:
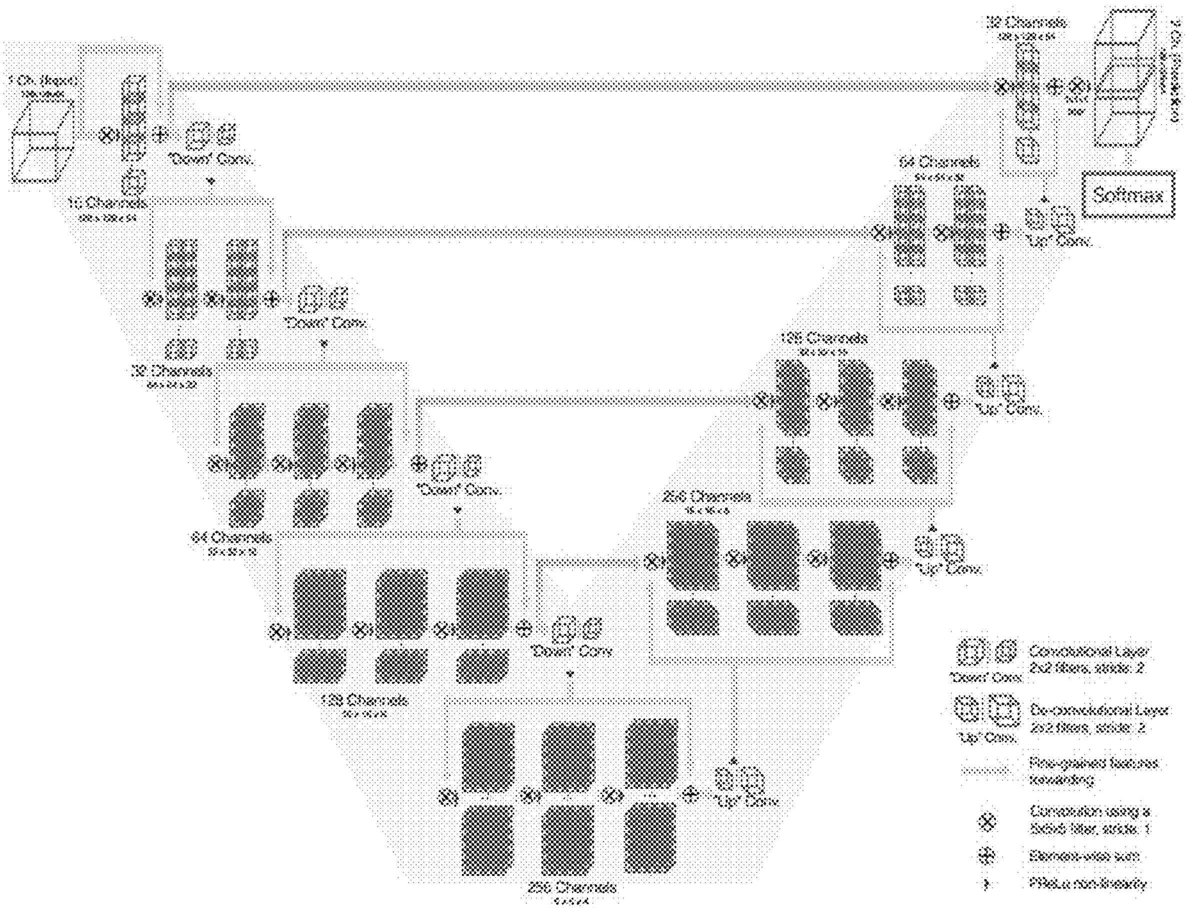
FIG. 4 illustrates an example of a neural network that can be used to segment the scan data in the flowchart of FIG. 2.

FIG. 4 illustrates an example of a neural network that can be used to segment the scan data in the flowchart of FIG. 2. In the illustrated example, the neural network can comprise a "V-net" convolutional neural network. As described in FIG. 2, the method can include the usage of at least three different 3D neural networks, which provides full semantic segmentation of the 3D scan (e.g., individual teeth segmentation, upper bone segmentation, and lower bone segmentation).

Referring back to FIG. 1C, a diagram is shown that includes an example of the 3D fusion engine(s) **162*a*. The 3D fusion engine(s) 162*a* may include a feature alignment engine 178, a bone preprocessing engine 180, a tooth numbering engine 182, and a merged dental model datastore 184. One or more of the modules of the 3D fusion engine(s) 162*a*** may be coupled to each other or to modules not shown.

The feature alignment engine 178 may implement one or more automated agents configured to align and merge segmented scan data from the scan segmentation engine(s) 160 with a digital 3D dental treatment plan. A digital 3D dental treatment plan may be generated during the course of a dental treatment for a patient. The dental treatment plan can comprise a three-dimensional model, such as a 3D mesh model or a 3D point cloud, that may be generated from a scan, such as an intraoral scan, of the patient's teeth. This dental treatment plan includes information may be used to simulate, modify and/or choose between various orthodontic treatment plans. The feature alignment engine 178 is configured to add segmented 3D scan data (such as segmented data from a 3D CT scan, CBCT scan, or MRI scan) to be added to the 3D dental treatment plan. It is assumed that the 3D scan is segmented with some different software than the dental treatment plan software, and the segmentation result is provided as 3D array of teeth and bone labels with scale information. The feature alignment engine automatically aligns segmented 3D scan data and populates the digital dental plan with realistic root and bone surfaces.

The feature alignment engine 178 can first produce a coarse alignment of segmented 3D scan data with the digital treatment plan. In one implementation, this coarse alignment can be based on a comparison of tooth crowns from the digital dental model with each corresponding segmented tooth volume from the segmented 3D scan. The feature alignment engine 178 can compute vectors from the center of jaw teeth to the center of opposite jaw teeth in the segmented 3D scan. Using these vectors, the system can find the most prominent "tip" point on each tooth of the segmented 3D scan. These "tip" points can be aligned with corresponding points in the digital dental treatment plan. The feature alignment engine 178 can then produce a fine alignment of the segmented 3D scan data with the digital treatment plan. This can be done with, for example, an iterative closest point (ICP) algorithm.

Figure 5A:
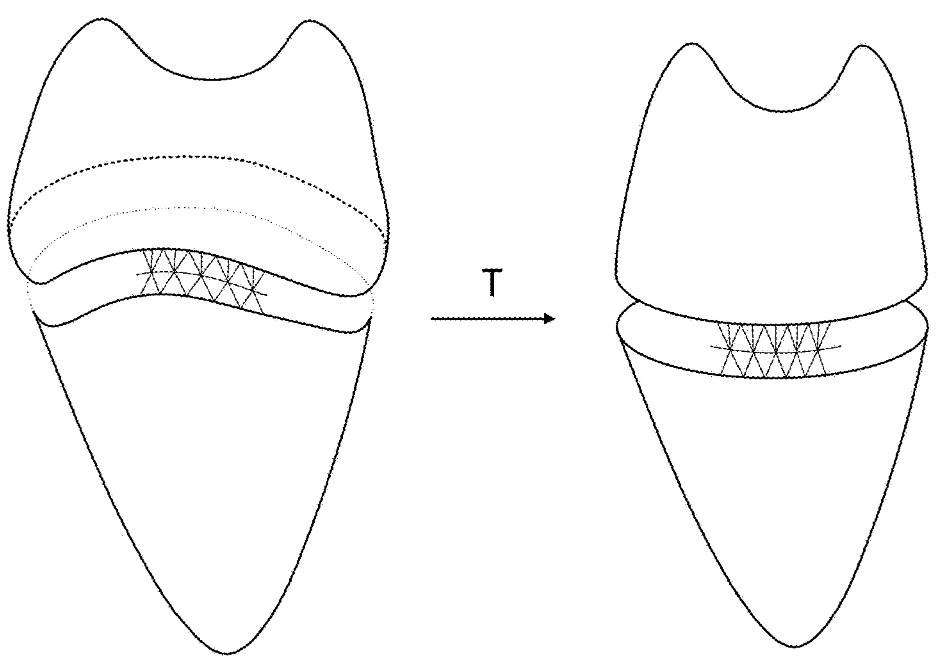
FIG. 5A illustrates one example of stitching segmented 3D scan roots to digital treatment plan tooth crowns.

The feature alignment engine 178 can further be configured to stitch tooth crowns from the digital dental treatment plan with tooth roots from the segmented 3D scan. Segmented 3D scan data (such as from a CBCT scan) typically includes both root and crown areas. However, the resolution of tooth areas from 3D scans is often much worse than the resolution of intraoral scans used for reconstruction of crowns in a digital dental treatment plan. The feature alignment engine 178 can therefore be configured to stitch low-res segmented 3D scan root data to crown data in the digital dental treatment plan. The goal of a root stitching procedure is a reduction of non-anatomic artifacts along the stitching line. Those artifacts are surface steps, gaps, and/or local topology changes. In one implementation, the feature alignment engine 178 provides a "straightening" of the LAT line in some auxiliary space P with coordinates (x, y, z). A generic straightening transformation T takes uniformly distributed LAT points to some uniformly distributed points on a 2D circle S: ($x^2+y^2$=const, z=0), takes crown points to semi-space z>0, and takes root points to semi-space z<0. Transformation T can be a Thin Plate Spline (TPS) defined by control points uniformly distributed on the LAT line and their images, uniformly distributed on circle S. The stitching of tooth crowns with tooth roots is illustrated in FIG. 5A. The stitching procedure can be implemented in a digital orthodontic treatment planning software and can be displayed to a user of the software, such as on a monitor or display.

The bone preprocessing engine 180 is configured to provide necessary preprocessing of 3D scan surfaces for reduction of digital noise and suppression of potential segmentation errors. In one implementation, the bone preprocessing engine is configured to patch teeth sockets in the digital dental model. Once the teeth sockets are patched, semitransparent bone can be shown over planned teeth movement without visual interference of moving root contours and unmovable socket contours. This can be displayed to a user, for example, a user of a digital orthodontic treatment planning software. Socket zones can be detected as parts of bone surface which are close enough to some 3D scan teeth surfaces. Socket zones can be removed from bone surfaces by the bone preprocessing engine and the remaining holes can be filled with smooth patches. In one implementation, the bone preprocessing engine 180 can produce filtration of small connected components and some generic smoothing of the surfaces. The socket/teeth patching described above is illustrated in FIG. 5B.

The tooth numbering engine 182 can be configured to number and/or renumber individual teeth in the digital dental treatment plan. It should be noted that teeth numbering in the digital dental treatment plan and teeth numbering from the segmented 3D scan can be different. One typical reason is missed teeth. For example, if the first premolar is actually missing, automatic 3D scan segmentation can incorrectly guess that second premolar is missed instead of the first premolar. ICP surface matching can therefore be used to ignore teeth numbering and provide correct alignment for such cases. This process assumes that teeth numbering in the digital dental treatment plan are correct, and updates teeth numbering in the scanned 3D segmentation.

The merged dental model datastore 184 may be configured to store data related to the alignment between the segmented 3D scan and the digital dental model, the tooth/socket patching from the bone preprocessing engine, and/or the tooth numbering data from the modules described above.

Figure 6:
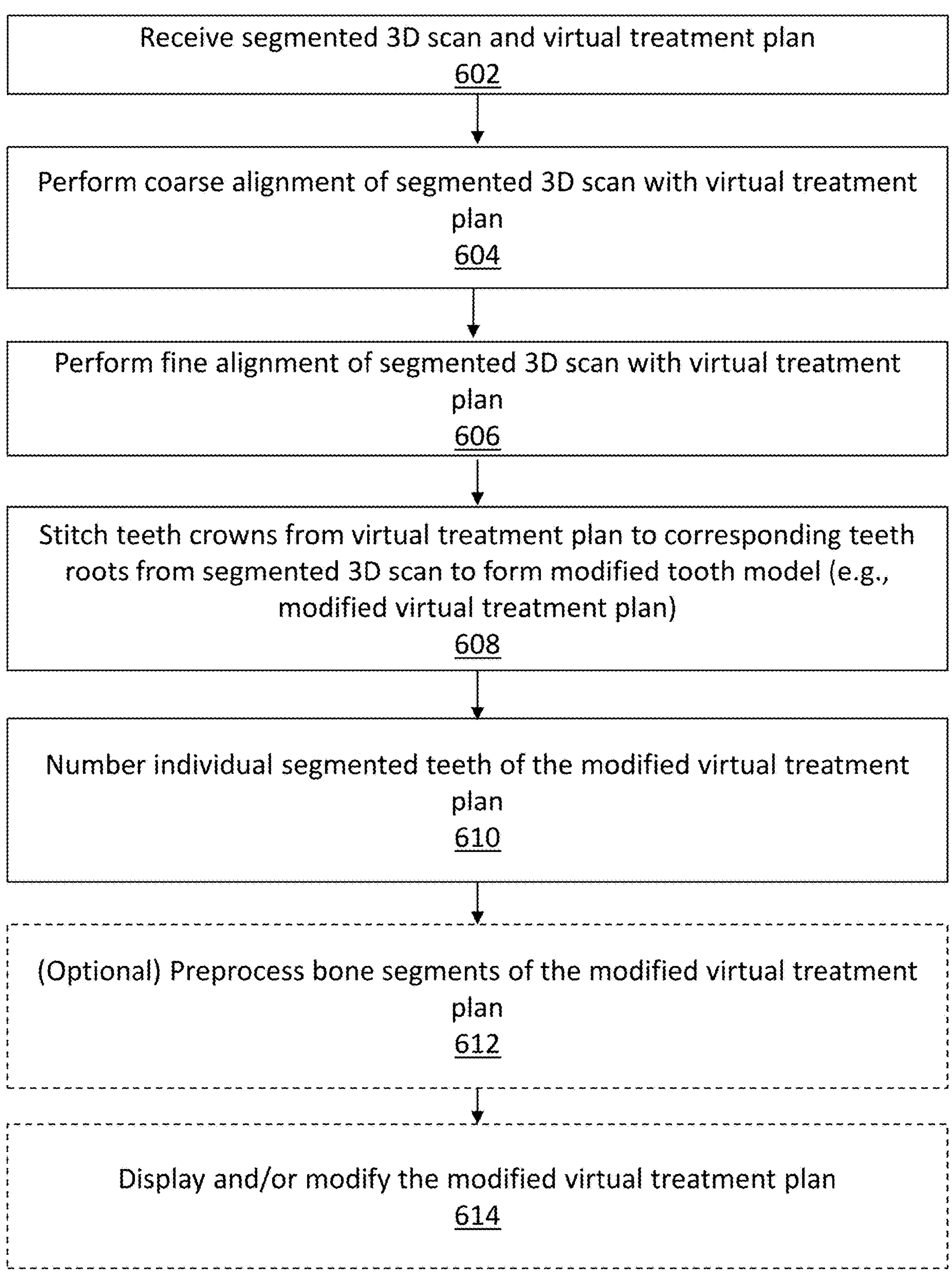
FIG. 6 illustrates one example of a method for adding segmented 3D scan data, such as a from a CT scan, a CBCT scan, or a MRI scan, to a digital dental treatment plan that includes a 3D dental model of the patient's teeth.

FIG. 6 illustrates one example of a method for adding segmented 3D scan data, such as a from a CT scan, a CBCT scan, or an MRI scan, to a digital dental treatment plan that includes a 3D dental model of the patient's teeth. This method may be automatically implemented by a system, such as one or more of the systems in the computing environment 100A, shown in FIG. 1A. This method may also be automatically implemented in the 3D fusion engine(s) 162 of FIG. 1A, and in the 3D fusion engine(s) 162*a* of FIG. 1C.

At an operation 602, the system can automatically receive segmented 3D scan data and a virtual treatment plan or digital dental treatment plan for a patient. As described above, the segmented 3D scan data can be a fully segmented CT scan, CBCT scan, or MRI scan, and the digital dental treatment plan can be a 3D mesh or 3D point cloud representing the patient's dentition and the digital plan for how to modify the patient's teeth to obtain a desired dental result.

At an operation 604, the system can perform a coarse alignment of the segmented 3D scan with the virtual treatment plan. The coarse alignment can be based on a comparison of tooth crowns from the digital dental model with each corresponding segmented tooth volume from the segmented 3D scan. Features such as "tips" of the segmented 3D scan can be aligned with corresponding features in the digital dental treatment plan.

At an operation 606, the system can perform a fine alignment of the segmented 3D scan with the virtual treatment plan. The fine alignment can be achieved by performing an iterative closest point (ICP) algorithm, for example.

At an operation 608, the system can be configured to stich tooth crowns from the digital dental treatment plan with tooth roots from the segmented 3D scan. The result of this operation is the stitching of low resolution tooth roots from the 3D scan with the high resolution of tooth crowns from an intraoral scan (used to generate the digital dental treatment plan). In one implementation, artifacts along the stitching line between the roots and crowns can be reduced or removed.

At an operation 610, the system can be configured to number and/or renumber individual teeth in the digital dental treatment plan. In one implementation, the system assumes that tooth numbering in the digital dental treatment plan is correct and updates the segmented 3D scan data to reflect the tooth numbering from the digital dental treatment plan.

Figure 5B:
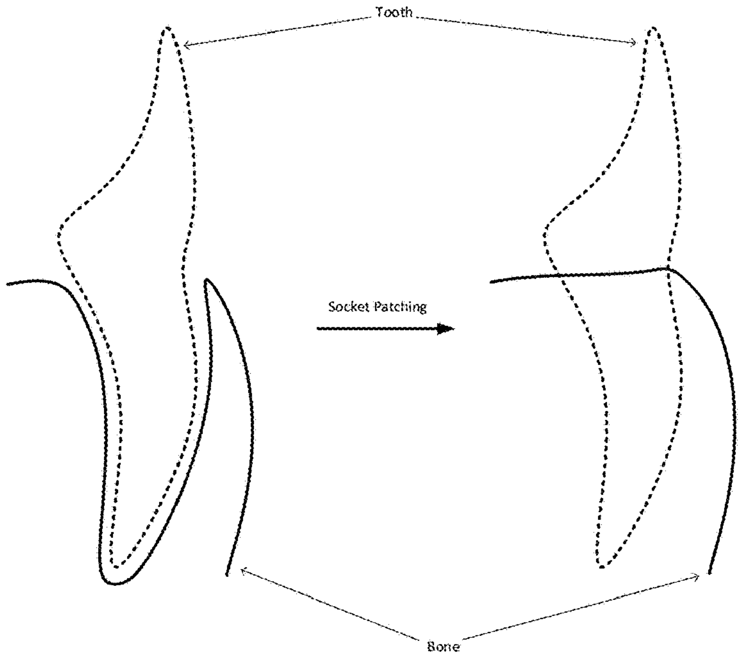
FIG. 5B is one example of an automated process for socket patching in a dental model.

The method or system may be configured to pre-process bone segments of the modified virtual treatment plan, e.g., to patch (e.g., remove/smooth) of teeth sockets, as described in FIG. 5B. Once the teeth sockets are patched, semitransparent bone could be shown over planned teeth movement without visual interference of moving root contours and unmovable socket contours. Socket zones may be detected as parts of bone surface which are close enough to some teeth surfaces (e.g., in a CBCT scan or other root scan). Socket zones may be removed from bone surface and the remaining holes are filled with smooth patches. The bone surface may also be filtered for small, connected components and to provide generic smoothing. The resulting modified virtual treatment plan may be displayed 614 (or further modified).

Referring back to FIG. 1D, a diagram is shown that includes an example of the tooth modeling engine(s) 164*a*. The tooth modeling engine(s) 164*a* may include a generic tooth engine 186, a transformation engine 188, and a tooth modeling datastore 190. One or more of the modules of the tooth modeling engine(s) 164*a* may be coupled to each other or to modules not shown.

The generic tooth engine 186 may implement one or more automated agents configured to fit a generic tooth model into segmentation data from a segmented 3D scan. As described above, segmentation of 3D scans (such as CT scans, CBCT scans, MRI scans, etc.) can be performed on lower-resolution, resampled arrays, to fit the available fast and expensive memory on a GPU device. As a result, segmented details of the 3D scan can have noisy or low resolution surfaces. To overcome these deficiencies in segmented 3D scans, the generic tooth engine can be configured to use the segmentation data from the segmented 3D scan as auxiliary reference data, and fit into this data generic tooth models corresponding to the segmented teeth. Generic tooth models can constructed, for example, in accordance with U.S. Pat. No. 7,844,429, which is incorporated herein by reference in its entirety. A generic tooth is a template of tooth of corresponding type (cuspid, incisor, premolar, etc.), and can be constructed in advance, using plurality of mesh-based models specific to that particular tooth, observed on different patients, and having special landmark points, (e.g., a set of 3D points that allow reconstructing the 3D mesh with desired resolution and characteristics, such as form, smoothness and so on). The generic tooth engine 186 can be configured to match an appropriate generic tooth model to the 3D scan segmentation data. In one implementation, the generic tooth engine can select a portion of a segmented 3D scan, such as an individually segmented tooth in the segmented 3D scan. The generic tooth engine can then select a corresponding generic tooth model to the selected tooth, and fit the generic tooth model into the segmentation data.

The transformation engine 188 may implement one or more automated agents configured to adjust the position and orientation of the generic tooth model to better match the position and orientation of the selected segmented tooth from the 3D scan data. The generic tooth model can be adjusted by adding or modifying several or all control points of the generic tooth model. In one implementation, adding control points can include finding apex positions in the segmentation data from the 3D scan for a particular tooth, overlaying contours of the generic tooth model onto the segmentation data, identifying discrepancies between the segmentation data and the generic tooth model, computing coordinates of points along the discrepancies, and adding one or more control points to the generic tooth model at these computed coordinates. The control points allow for the manipulation of the position/orientation of the generic tooth model. The adjusted generic tooth model can then be transformed into the segmented 3D scan (or into a digital dental treatment plan).

The tooth modeling datastore 190 may be configured to store data related to the data from the modules described above, including generic tooth model data, 3D control point data, and transformation data of the generic tooth model into the segmented 3D scan or into the digital dental treatment plan.

Figure 7:
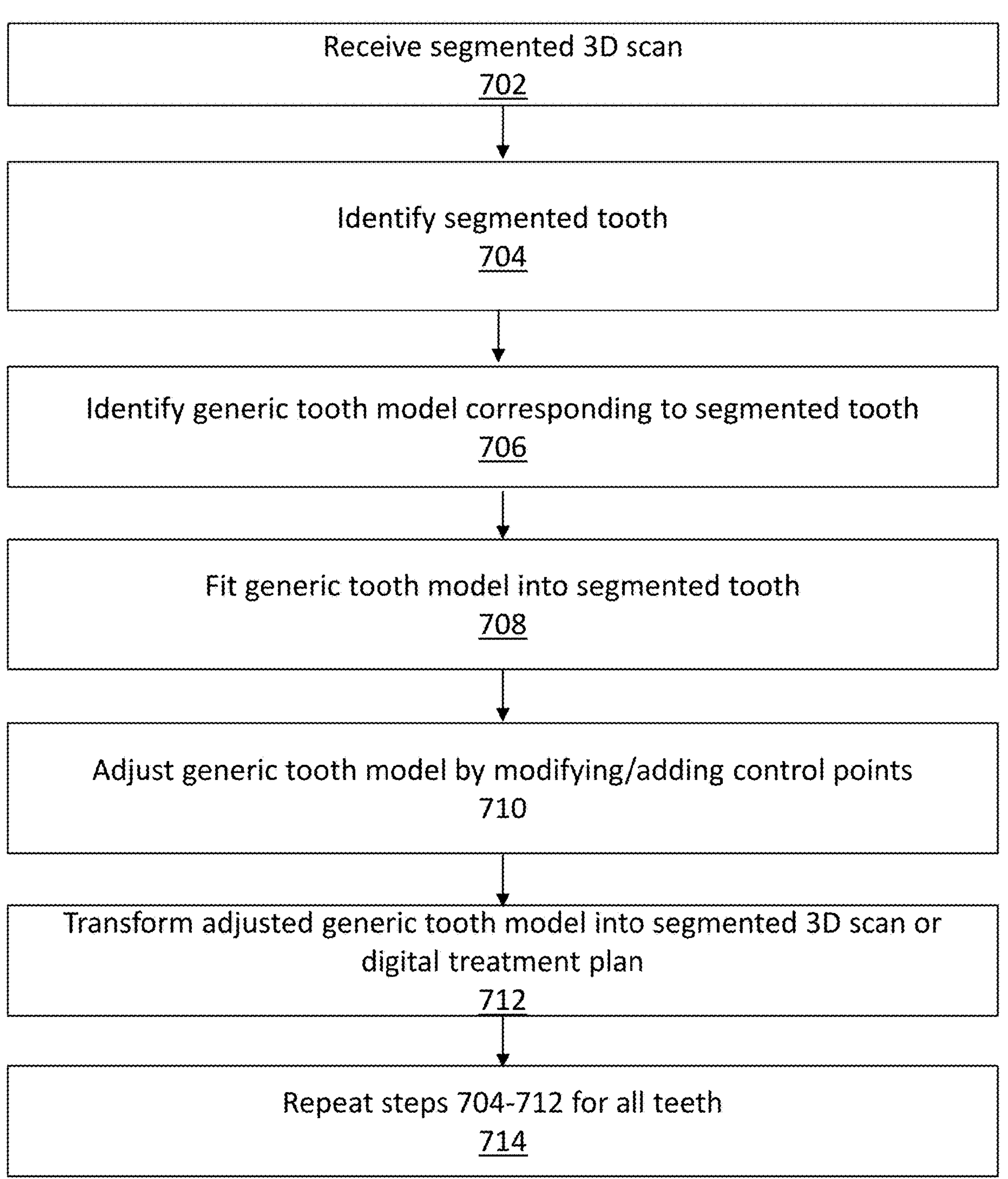
FIG. 7 illustrates one example of a method for modeling complete tooth to patient crowns and roots.

FIG. 7 illustrates one example of a method for modeling complete tooth to patient crowns and roots. This method may be automatically implemented by a system, such as one or more of the systems in the computing environment 100A, shown in FIG. 1A. This method may also be automatically implemented in the tooth modeling engine(s) 164 of FIG. 1A, and in the tooth modeling engine(s) 164*a* of FIG. 1D.

At an operation 702, the system can receive a segmented 3D scan data for a patient. As described above, the segmented 3D scan data can be a fully segmented CT scan, CBCT scan, or MRI scan.

Figure 8A:
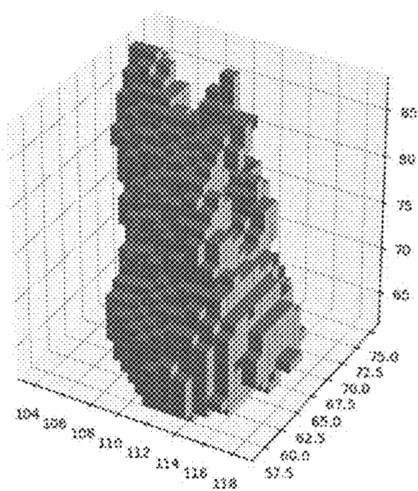
FIG. 8A is an illustration showing one example of a segmented tooth from a segmented 3D scan, having a low resolution.

At an operation 704, the system can identify a portion of the segmented 3D scan, such as an individually segmented tooth. As described above, segmentation of 3D scans (such as CT scans, CBCT scans, MRI scans, etc.) can be performed on lower-resolution, resampled arrays, to fit the available fast and expensive memory on a GPU device. As a result, segmented details of the 3D scan can have noisy or low resolution surfaces. FIG. 8A is an illustration showing one example of a segmented tooth from a segmented 3D scan, having a low resolution.

Figure 8B:
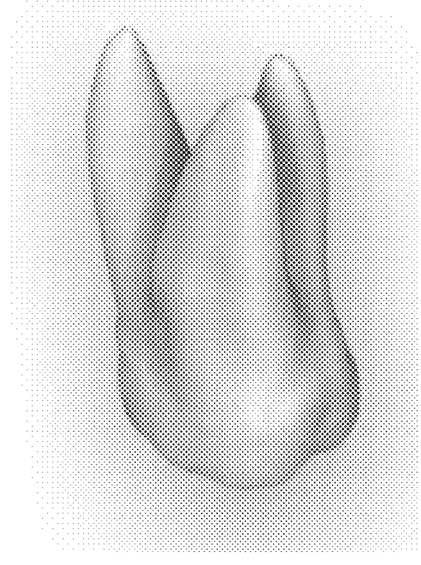
FIG. 8B is an example of a generic tooth model corresponding to the segmented tooth from FIG. 8A.

At an operation 706, the system can be configured to identify a generic tooth model corresponding to the segmented tooth selected at operation 704. As described above, a generic tooth model is a template of tooth of corresponding type (cuspid, incisor, premolar, etc.), and can be constructed in advance, using plurality of mesh-based models specific to that particular tooth, observed on different patients, and having special landmark points, (e.g., a set of 3D points that allow reconstructing the 3D mesh with desired resolution and characteristics, such as form, smoothness and so on). In one implementation, the selected generic tooth model can be based on the tooth numbering assigned to the selected tooth during segmentation. In other implementations, the selection of the generic tooth model can be based on features of the selected segmented tooth (e.g., shapes, features of interest, points, size of the tooth, etc.). FIG. 8B is an example of a generic tooth model corresponding to the segmented tooth from FIG. 8A.

At an operation 708, the generic tooth model can be fit into the segmentation data corresponding to the selected tooth. At an operation 710, the generic tooth model can be adjusted by modifying or adding control points to the generic tooth model. These control points can then be adjusted or transformed to adjust the shape, position, and/or orientation of the generic tooth model to better fit into the segmentation data for the selected tooth.

At an operation 712, the adjusted generic tooth model can be transformed into the segmented 3D scan or into a digital dental treatment plan or dental model. As described above, a digital orthodontic treatment planning software can be used to generate a 3D dental model or digital dental treatment plan. This digital dental treatment plan At an operation 714, the operations 704 to 712 can be repeated for some or all of the segmented teeth from the segmented 3D scan.

Figure 9:
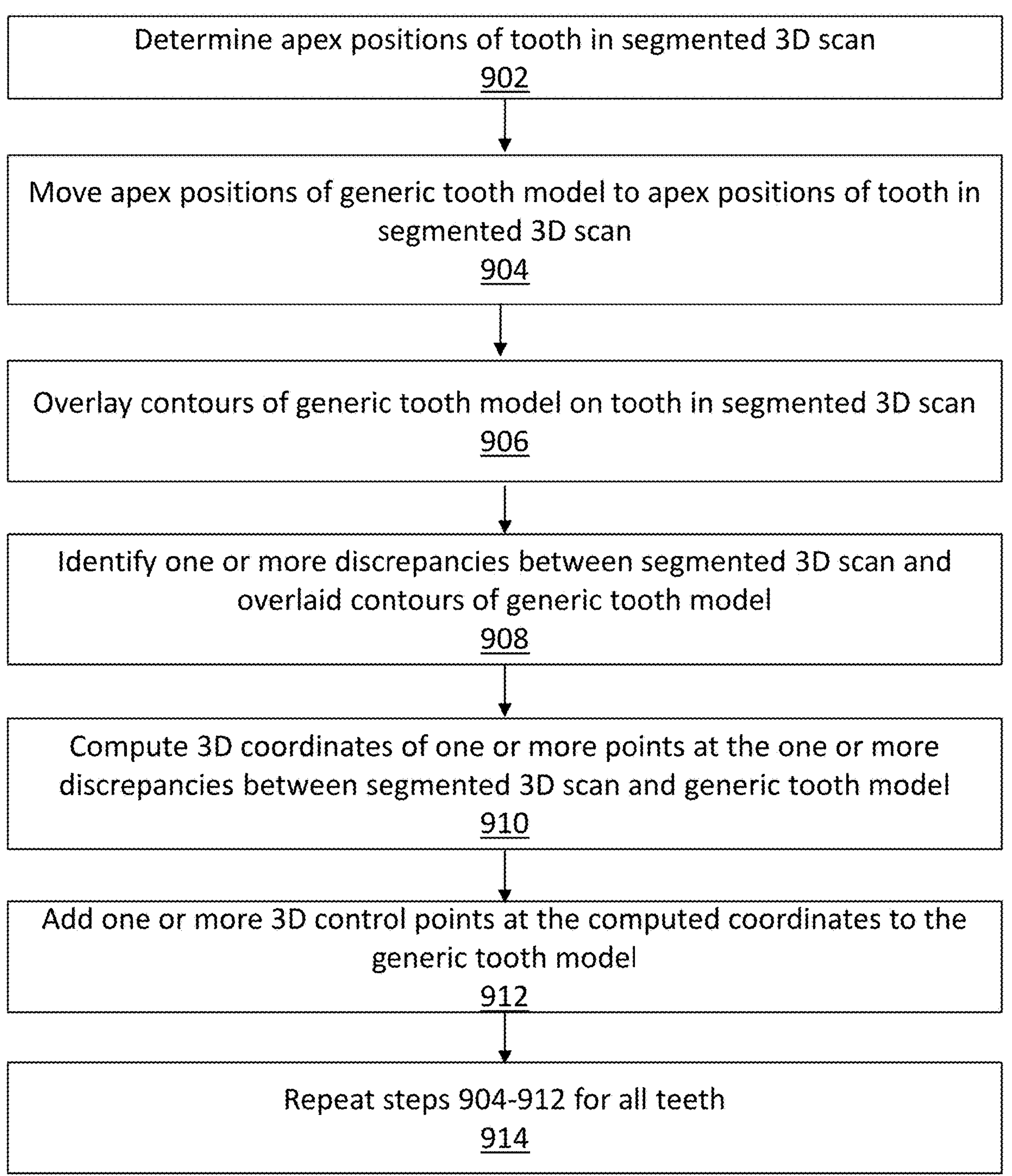
FIG. 9 illustrates one example of a method for adjusting a generic tooth model to better fit into a segmented tooth from a 3D scan.

FIG. 9 illustrates one example of a method for adjusting a generic tooth model to better fit into a segmented tooth model. The flowchart of FIG. 9 expands upon operation 710 described in the flowchart of FIG. 7. This method may be automatically implemented by a system, such as one or more of the systems in the computing environment 100A, shown in FIG. 1A. This method may also be automatically implemented in the tooth modeling engine(s) 164 of FIG. 1A, and in the tooth modeling engine(s) 164*a* of FIG. 1D.

As described above in the flowchart of FIG. 7, it is desirable to transform/adjust the generic tooth model to better fit into the segmented tooth data from the segmented 3D scan. Operation 710 of FIG. 7 recites the step of adjusting the generic tooth model by modifying/adding control points to the generic tooth model.

At operations 902 and 904, the system can find the apex positions on the segmented 3D scan corresponding to the selected tooth and move the apexes of the generic tooth to those positions.

Next, at an operation 906, the system can overlay contours of the generic tooth model on the selected tooth in the segmented 3D scan.

Figure 10A:
FIG. 10A illustrates a generic tooth model overlaid upon the segmented 3D scan with the discrepancies between the model and the scan identified.

At an operation 908, the system can identify one or more discrepancies between the selected tooth of the segmented 3D scan and the overlaid contours of the generic tooth model. FIG. 10A illustrates a generic tooth model overlaid upon the segmented 3D scan with the discrepancies between the model and the scan identified. The discrepancies between the selected tooth of the segmented 3D scan and the overlaid contours of the generic tooth model can be displayed to a user of a digital orthodontic treatment planning software on a monitor or display.

Figure 10B:
FIG. 10B illustrates an example of a point positioned along the edge of a discrepancy between the selected segmented tooth in the 3D scan and the generic tooth model.

At an operation 910, the system can compute 3D coordinates of one or more points at the one or more discrepancies between the segmented 3D scan and the overlaid generic tooth model. FIG. 10B illustrates an example of a point positioned along the edge of a discrepancy between the selected segmented tooth in the 3D scan and the generic tooth model.

At an operation 912, the system can be configured to add one or more 3D control points at the computed coordinates from operation 910 to the generic tooth model. The 3D control points then allow for manipulation and adjustment of the position, orientation, size, and shape of the generic tooth model.

At operation 914, the steps outlined in operations 904-912 can be repeated for some or all of the segmented teeth from the segmented 3D scan.

Figure 1E:
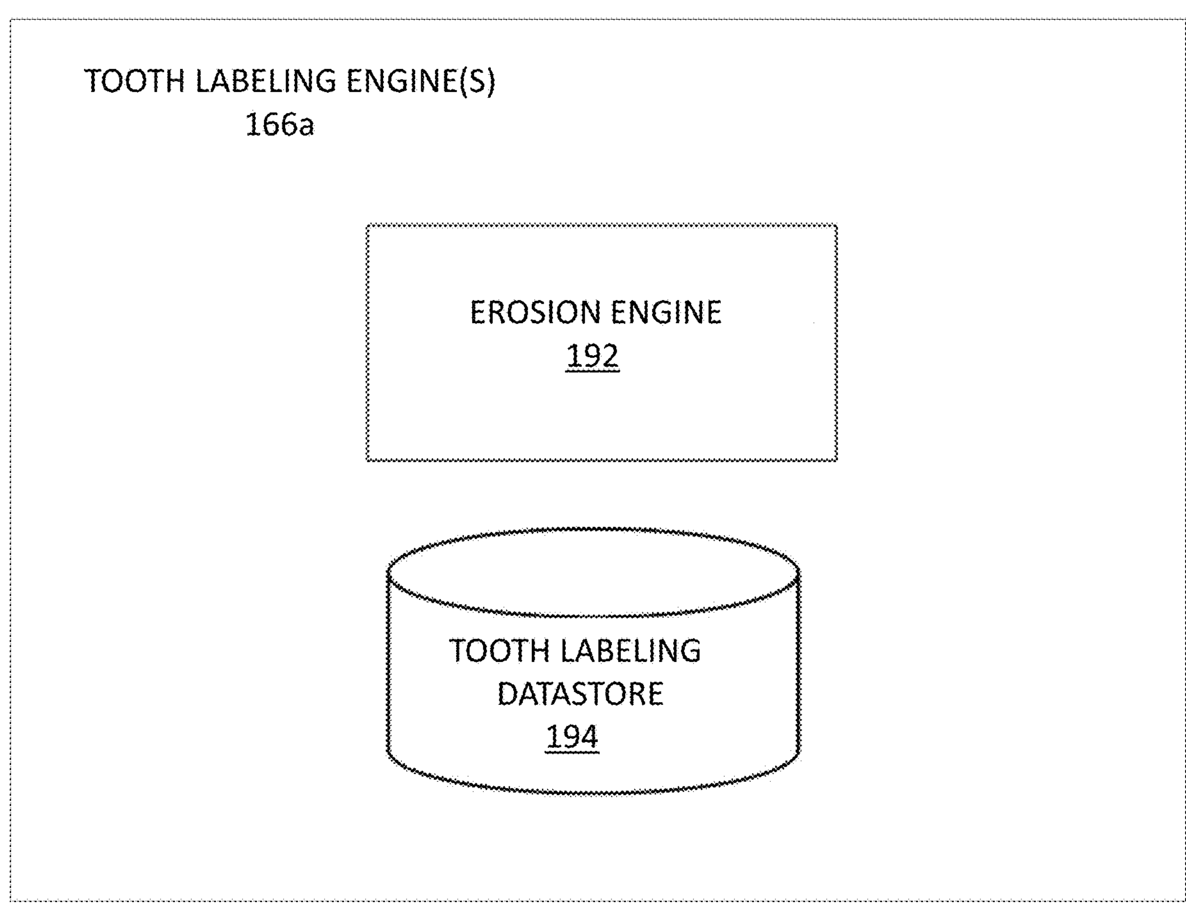
FIG. 1E is a diagram showing an example of a tooth labeling engine(s).

Referring back to FIG. 1E, a diagram is shown that includes an example of the tooth labeling engine(s) 166*a*. The tooth labeling engine(s) 166*a* may include an erosion engine 192 and a tooth labeling datastore 194. One or more of the modules of the tooth labeling engine(s) 166*a* may be coupled to each other or to modules not shown.

The erosion engine 192 may implement one or more automated agents configured to individually number/label segmented teeth in a segmented 3D scan. In one implementation, the erosion engine 192 receives as an input a binary volume of teeth (label map) received after automatic segmentation of a 3D scan (such as segmentation of a CT scan, a CBCT scan, or a MRI scan as described above). The erosion engine 192 may be configured to separate the label map with a watershed algorithm. In one implementation, seeds for the watershed algorithm are formed through iterations of erosion, applied to the label map. These seeds take into account the morphological structure of teeth during the seeds preparation, thus increasing the quality of volume separation. The seeds can be applied to the original binary label map, and the watershed algorithm can be applied again to segment the individual teeth into separate components for more accurate labeling.

The tooth labeling datastore 194 may be configured to store data related to the data from the modules described above, including the labeling/numbering data, erosion data, and seed data as described herein.

Figure 11:
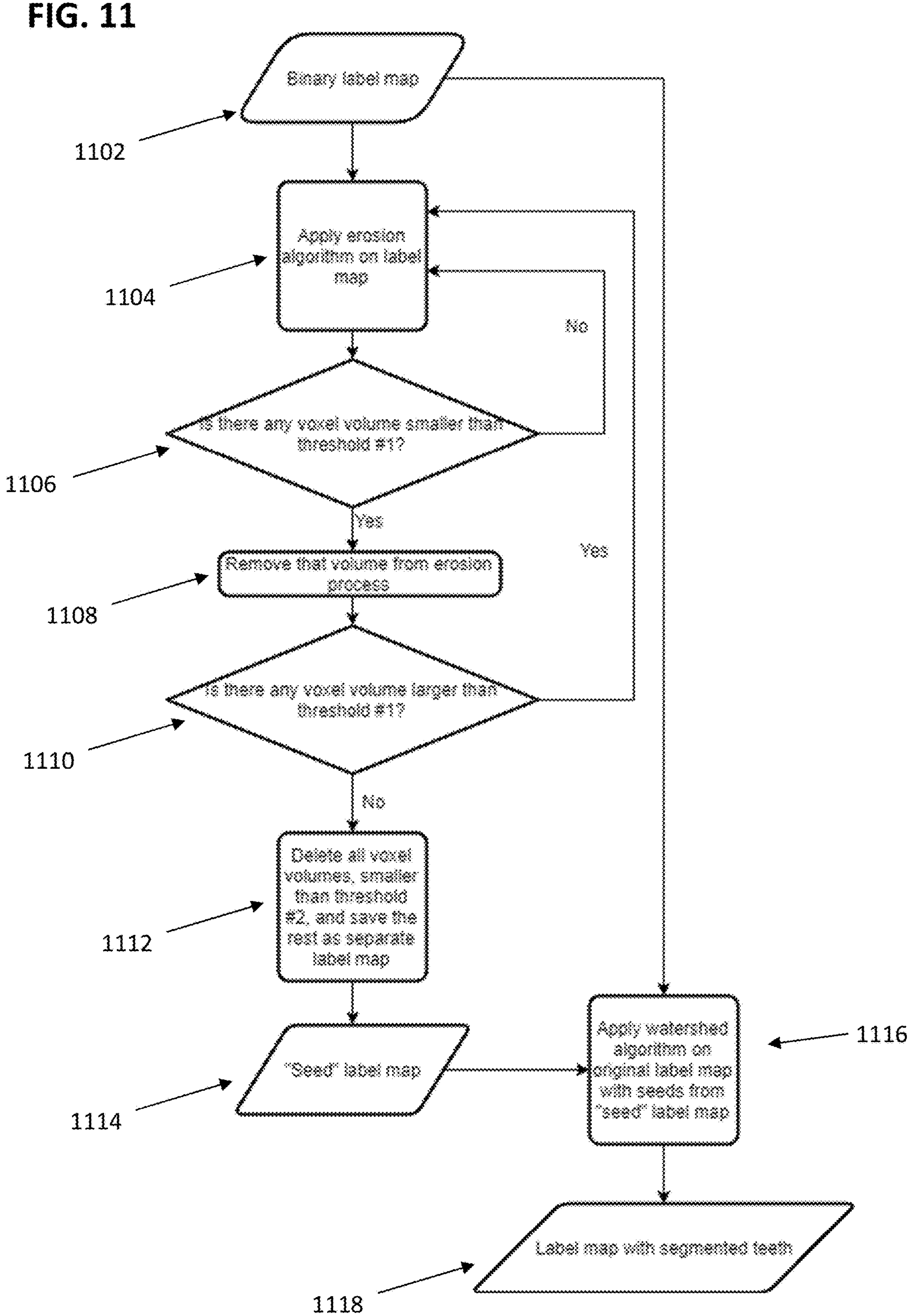
FIG. 11 is a flowchart describing a method of segmenting teeth.

FIG. 11 illustrates one example of a method for numbering segmented teeth in a segmented 3D scan. This method may be automatically implemented by a system, such as one or more of the systems in the computing environment 100A, shown in FIG. 1A, or by a digital orthodontic treatment planning software implemented in a computing system such as a personal computer, tablet, or smartphone. This method may also be automatically implemented in the tooth labeling engine(s) 166 of FIG. 1A, and in the tooth labeling engine(s) 166*a* of FIG. 1E.

Figure 12A:
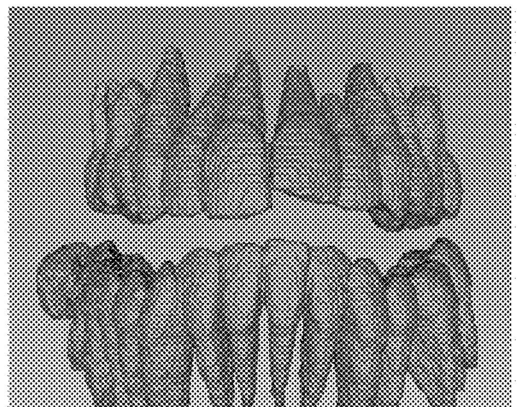
FIG. 12A is an example of an original label map.

At an operation 1102, the system can input a binary label map, such as a binary label map from a segmented 3D scan (e.g., a segmented CT scan, CBCT scan, or MRI scan). An example of an original label map is shown in FIG. 12A.

Figure 12B:
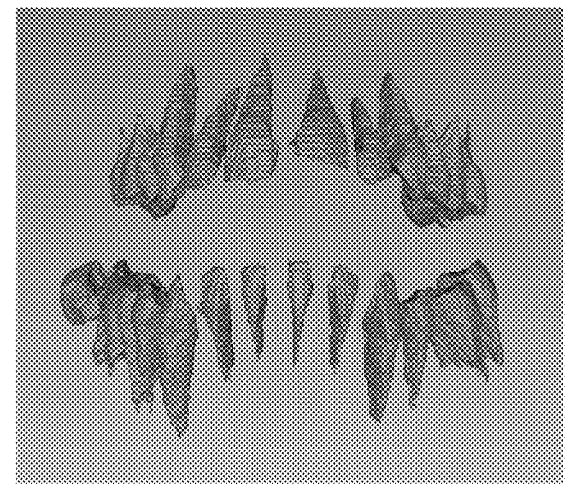
FIG. 12B illustrates an example of a binary label map after 6 iterations of erosion.
Figure 12C:
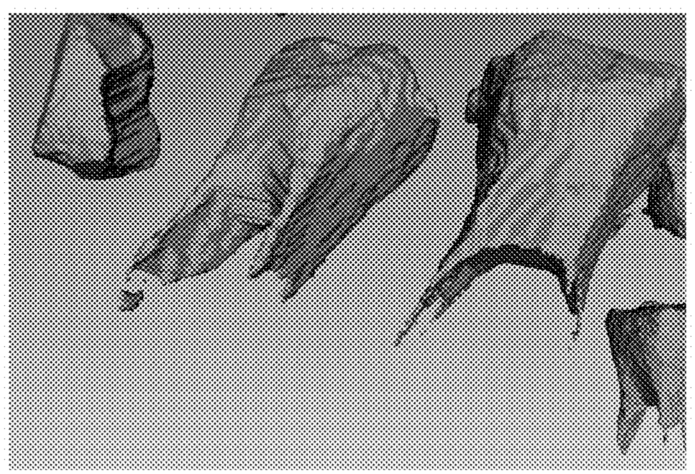
FIG. 12C illustrates a binary map with voxel volumes smaller than a first threshold.
Figure 12D:
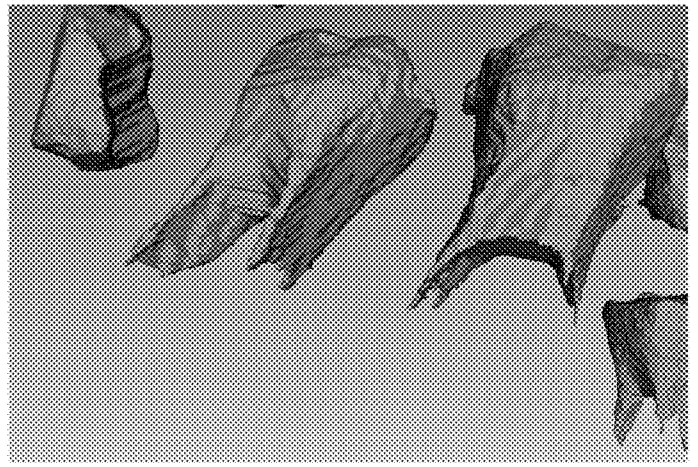
FIG. 12D shows the binary map with those voxel volumes removed.

At an operation 1104, the system can apply an erosion algorithm on the binary label map from operation 1102. At operation 1106, the system checks if there are any voxel volumes smaller than a first threshold voxel volume. At operation 1108, these voxel volumes smaller than the first threshold voxel volume are removed from the erosion process. FIG. 12C illustrates a binary map with voxel volumes smaller than a first threshold, and FIG. 12D shows the binary map with those voxel volumes removed. Operations 1104-1108 are repeated until there are no longer any voxel volumes larger than the first threshold volume. FIG. 12B illustrates an example of a binary label map after 6 iterations of erosion.

Next, at an operation 1112, all voxel volumes smaller than a second threshold are removed, and the remaining voxel volumes are saved as seeds in a separate label map.

Figure 13A:
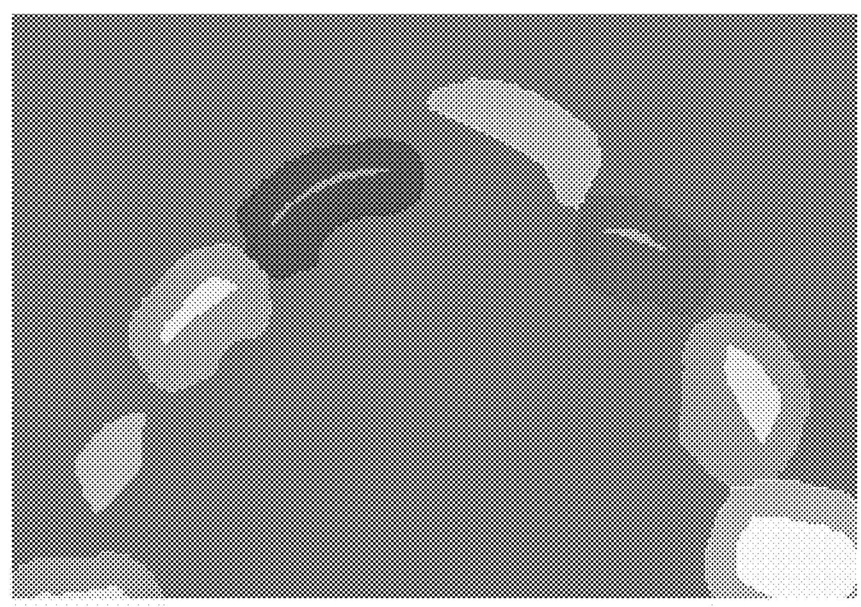
FIG. 13A is an illustration of a binary label map seeded with seeds from an erosion algorithm.

At an operation 1114, the binary label map from operation 1102 is seeded with the "seeds" from operation 1112. FIG. 13A is an illustration of a binary label map seeded with seeds from operation 1114.

Figure 13B:
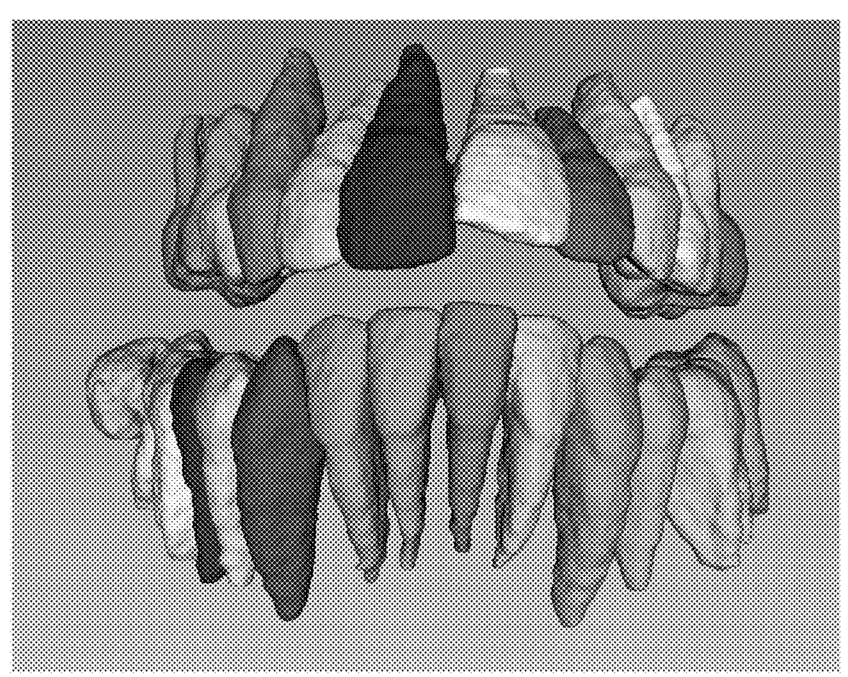
FIG. 13B is an example of a segmented and scanned 3D scan.

At operation 1116, the watershed algorithm is applied to the seeded map from operation 1114. The output at operation 1118 is a label map with fully segmented and labeled teeth. This fully segmented and labeled map is illustrated in FIG. 13B.

Figure 14:
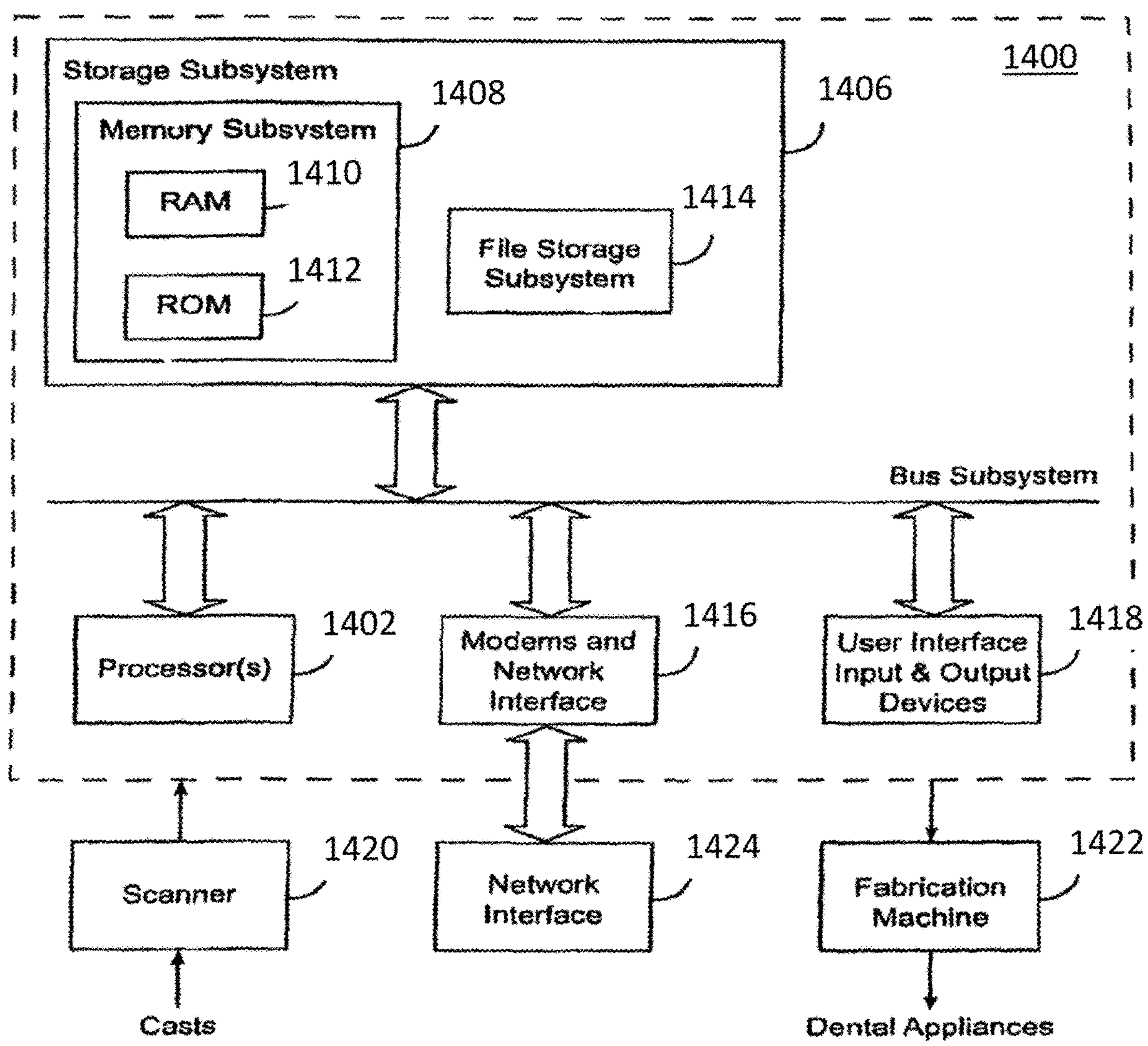
FIG. 14 is a simplified block diagram of a data processing system that may perform the methods described herein.

The methods described herein may be performed by an apparatus, such as a data processing system, which may include hardware, software, and/or firmware for performing many of these steps described above. For example, FIG. 14 is a simplified block diagram of a data processing system 1400. Data processing system 1400 typically includes at least one processor 1402 which communicates with a number of peripheral devices over bus subsystem 1404. These peripheral devices typically include a storage subsystem 1406 (memory subsystem 1408 and file storage subsystem 1414), a set of user interface input and output devices 1418, and an interface to outside networks 1416, including the public switched telephone network. This interface is shown schematically as "Modems and Network Interface" block 1416, and is coupled to corresponding interface devices in other data processing systems over communication network interface 1424. Data processing system 1400 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 1406 maintains the basic programming and data constructs that provide the functionality of the present invention. The software modules discussed above are typically stored in storage subsystem 1406. Storage subsystem 1406 typically comprises memory subsystem 1408 and file storage subsystem 1414.

Memory subsystem 1408 typically includes a number of memories including a main random access memory (RAM) 1410 for storage of instructions and data during program execution and a read only memory (ROM) 1412 in which fixed instructions are stored. In the case of Macintosh-compatible personal computers the ROM would include portions of the operating system; in the case of IBM-compatible personal computers, this would include the BIOS (basic input/output system).

File storage subsystem 1414 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term “bus subsystem” is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 1404 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 1420 is responsible for scanning casts of the patient's teeth obtained either from the patient or from an orthodontist and providing the scanned digital data set information to data processing system 1400 for further processing. In a distributed environment, scanner 1420 may be located at a remote location and communicate scanned digital data set information to data processing system 1400 over network interface 1424.

Fabrication machine 1422 fabricates dental appliances based on intermediate and final data set information acquired from data processing system 1400. In a distributed environment, fabrication machine 1422 may be located at a remote location and acquire data set information from data processing system 1400 over network interface 1424.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being “on” another feature or element, it can be directly on the other feature or element or intervening features and/or elements may also be present. In contrast, when a feature or element is referred to as being “directly on” another feature or element, there are no intervening features or elements present. It will also be understood that, when a feature or element is referred to as being “connected”, “attached” or “coupled” to another feature or element, it can be directly connected, attached or coupled to the other feature or element or intervening features or elements may be present. In contrast, when a feature or element is referred to as being “directly connected”, “directly attached” or “directly coupled” to another feature or element, there are no intervening features or elements present. Although described or shown with respect to one embodiment, the features and elements so described or shown can apply to other embodiments. It will also be appreciated by those of skill in the art that references to a structure or feature that is disposed “adjacent” another feature may have portions that overlap or underlie the adjacent feature.

Terminology used herein is for the purpose of describing particular embodiments only and is not intended to be limiting of the invention. For example, as used herein, the singular forms “a”, “an” and “the” are intended to include the plural forms as well, unless the context clearly indicates otherwise. It will be further understood that the terms “comprises” and/or “comprising,” when used in this specification, specify the presence of stated features, steps, operations, elements, and/or components, but do not preclude the presence or addition of one or more other features, steps, operations, elements, components, and/or groups thereof. As used herein, the term “and/or” includes any and all combinations of one or more of the associated listed items and may be abbreviated as “/”.

Spatially relative terms, such as “under”, “below”, “lower”, “over”, “upper” and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, the method comprising:

receiving, in a computing device, scan data comprising a bone root scan of a patient's dentition;

segmenting the scan data into individual teeth, wherein the individual teeth include crowns and tooth roots, wherein the segmenting comprises:

forming a first segmented volume by segmenting a first portion of the scan data with a first segmentation process;

forming a second segmented volume by segmenting a second portion of the scan data with a second segmentation process, wherein the first segmented volume has a lower resolution than the second segmented volumes; and forming segmenting scan data by merging the first segmented volume with the second segmented volume, the merging comprising:

removing teeth labels from the first segmented volume;

adjusting a resolution of the first segmented volume to be the same as a resolution of the second segmented volume; and replacing voxels in the first segmented volume with voxels from the second segmented volume;

aligning the segmented scan data to a digital model of the patient's dentition;

modifying the digital model of the patient's dentition to include the tooth roots from the aligned segmented scan data to form a modified digital model; and displaying or modifying a treatment plan using the modified digital model.

2. The method of claim 1, wherein the bone root scan comprises a cone beam computed tomography (CBCT) scan.

3. The method of claim 1, wherein the bone root scan comprises one or more of: a cone beam computed tomography (CBCT) scan, a CT scan, and an MRI scan.

4. The method of claim 1, wherein segmenting the scan data comprises using a first neural network to segment the first portion of the scan data and a second neural network to segment the second portion of the scan data.

5. The method of claim 1, further comprising processing the aligned segmented scan data before modifying the digital model, wherein processing the aligned segmented scan data comprises patching teeth sockets from the aligned segmented scan data, wherein the teeth sockets correspond to parts of bone of the scan data where the individual teeth exist.

6. The method of claim 1, wherein the aligning comprises performing a coarse alignment and a fine alignment, wherein performing the fine alignment comprises applying an Iterative Closest Point (ICP), 3D matching algorithm.

7. The method of claim 1, further comprising smoothing the aligned segmented scan data.

8. The method of claim 1, further comprising processing the aligned segmented scan data to patch teeth sockets from the aligned segmented scan data, wherein patching the teeth sockets comprises removing tooth sockets, and displaying the modified digital model so that semitransparent representations of the bone are displayed over planned tooth movement without visual interference of moving root contours and unmovable socket contours.

9. The method of claim 1, wherein the aligning comprises a coarse alignment and a fine alignment, wherein the coarse alignment comprises determining the most prominent tip point of the crowns of each of the individual teeth using vectors from centers of the individual teeth to centers of teeth in an opposite jaw of the patient, and aligning the most prominent tip points of the crowns of the segmented scan data with corresponding tip points of the crowns of the digital model.

10. The method of claim 9, further comprising stitching the crowns of the digital model to corresponding tooth roots of the aligned segmented scan data.

11. The method of claim 10, wherein stitching the crowns of the digital model to the corresponding tooth roots of the aligned segmented scan data comprises straightening a stitching line of the aligned segmented scan data using a straightening transform.

12. The method of claim 1, wherein the first segmentation process is a binary segmentation process that categorizes pixels into two classes, wherein the second segmentation process is a multi-class segmentation process that categorizes pixels into more than two classes.

13. The method of claim 1, wherein the first segmentation volume comprises information associated with bones and the second segmentation volume comprises information associated with teeth.

14. A dental treatment system comprising:

one or more processors;

memory coupled to the one or more processors, the memory configured to store computer-program instructions that, when executed by the one or more processors, cause the one or more processors to execute a computer-implemented method, the computer-implemented method comprising:

receiving, in a computing device, scan data comprising a bone root scan of a patient's dentition;

segmenting the scan data into individual teeth, wherein the individual teeth include crowns and tooth roots, wherein the segmenting comprises:

forming a first segmented volume by segmenting a first portion of the scan data with a first segmentation process;

forming a second segmented volume by segmenting a second portion of the scan data with a second segmentation process, wherein the first segmented volume has a lower resolution than the second segmented volumes; and forming segmenting scan data by merging the first segmented volume with the second segmented volume, the merging comprising:

removing teeth labels from the first segmented volume;

adjusting a resolution of the first segmented volume to be the same as a resolution of the second segmented volume; and replacing voxels in the first segmented volume with voxels from the second segmented volume;

aligning the segmented scan data to a digital model of the patient's dentition;

modifying the digital model of the patient's dentition to include the tooth roots from the aligned segmented scan data to form a modified digital model; and displaying or modifying a treatment plan using the modified digital model.

15. The dental treatment system of claim 14, wherein the scan data is three-dimensional (3D) scan data and the digital model is a 3D digital model.

16. The dental treatment system of claim 14, wherein the aligning comprises determining the most prominent tip point of the crowns of each of the individual teeth using vectors from centers of the individual teeth to centers of teeth in an opposite jaw of the patient, and aligning the most prominent tip points of the crowns of the segmented scan data with corresponding tip points of the crowns of the digital model.

17. The dental treatment system of claim 16, wherein the computer-implemented method further comprises stitching the crowns of the digital model to corresponding tooth roots of the aligned segmented scan data.

18. The dental treatment system of claim 17, wherein stitching the crowns of the digital model to the corresponding tooth roots of the aligned segmented scan data comprises straightening a stitching line of the scan data using a straightening transform.

19. The dental treatment system of claim 14, further comprising displaying the modified digital model with semi-transparent representations of the bone over planned tooth movement without visual interference of moving root contours and unmovable socket contours.

20. The dental treatment system of claim 14, wherein the computer-implemented method further comprises processing the aligned segmented scan data before modifying the digital model, wherein processing the aligned segmented scan data comprises patching teeth sockets from the aligned segmented scan data, wherein the teeth sockets correspond to parts of bone of the scan data where the individual teeth exist.

21. The dental treatment system of claim 20, wherein the computer-implemented method further comprises displaying raw aligned segmented scan data for a user to review and correct the modified digital model.

22. The dental treatment system of claim 14, wherein the aligning comprises performing a coarse alignment and a fine alignment, wherein performing the fine alignment comprises applying an Iterative Closest Point (ICP), 3D matching algorithm.

23. The dental treatment system of claim 14, wherein the bone root scan comprises a cone beam computed tomography (CBCT) scan.

24. The dental treatment system of claim 14, wherein the bone root scan comprises a CT scan.

25. The dental treatment system of claim 14, wherein the bone root scan comprises an MRI scan.

26. The dental treatment system of claim 14, wherein segmenting the scan data comprises using a first neural network to segment the first portion of the scan data and a second neural network to segment the second portion of the scan data.

27. The dental treatment system of claim 14, wherein the first segmentation process is a binary segmentation process that categorizes pixels into two classes, wherein the second segmentation process is a multi-class segmentation process that categorizes pixels into more than two classes.

28. The dental treatment system of claim 14, wherein the first segmentation volume comprises information associated with bones and the second segmentation volume comprises information associated with teeth.

* * * * *